(12) United States Patent
Taylor et al.

(10) Patent No.: US 9,579,358 B2
(45) Date of Patent: Feb. 28, 2017

(54) COMPOSITIONS FOR BINDING TO AMYLOID PROTEINS

(71) Applicant: LANCASTER UNIVERSITY BUSINESS ENTERPRISES LIMITED, Lancaster, Lancashire (GB)

(72) Inventors: Mark Neville Taylor, Wigan (GB); David Allsop, Carnforth (GB)

(73) Assignee: LANCASTER UNIVERSITY BUSINESS ENTERPRISES LIMITED, Lancaster, Lancashire (GB)

( * ) Notice: Subject to any disclaimer, the term of this patent is extended or adjusted under 35 U.S.C. 154(b) by 77 days.

(21) Appl. No.: 14/350,912

(22) PCT Filed: Oct. 10, 2012

(86) PCT No.: PCT/GB2012/052513
§ 371 (c)(1),
(2) Date: Apr. 10, 2014

(87) PCT Pub. No.: WO2013/054110
PCT Pub. Date: Apr. 18, 2013

(65) Prior Publication Data
US 2014/0356418 A1 Dec. 4, 2014

(30) Foreign Application Priority Data

Oct. 10, 2011 (GB) .................................. 1117439.8
Feb. 15, 2012 (GB) .................................. 1202569.8

(51) Int. Cl.
| | | |
|---|---|---|
| A61K 31/08 | (2006.01) |
| A61K 38/08 | (2006.01) |
| A61K 47/48 | (2006.01) |
| A61K 38/10 | (2006.01) |

(52) U.S. Cl.
CPC .............. *A61K 38/08* (2013.01); *A61K 38/10* (2013.01); *A61K 47/48315* (2013.01); *A61K 47/48815* (2013.01)

(58) Field of Classification Search
None
See application file for complete search history.

(56) References Cited

U.S. PATENT DOCUMENTS

| 7,125,838 B1 | 10/2006 | Stott |
| 2009/0281036 A1 | 11/2009 | Meyer |
| 2010/0272714 A1* | 10/2010 | Acton et al. ............... 424/130.1 |
| 2011/0224133 A1* | 9/2011 | Jung et al. ..................... 514/3.7 |

FOREIGN PATENT DOCUMENTS

| WO | WO 01/07473 | 2/2001 |
| WO | WO 03/018609 | 3/2003 |
| WO | WO 2008/014917 | 2/2008 |

OTHER PUBLICATIONS

Mayo Clinic "Amyloidosis" (1998) Downloaded on Jun. 1, 2015, from http://www.mayoclinic.org/diseases-conditions/amyloidosis/basics/definition/con-20024354.*
Sciarretta et al (Methods Enzymol (2006) 413:273-312).*
Lee (Protein Science (Feb. 2009) 18(2): 277-286.*
Taylor 2011 (Nanomedicine: Nanotechnology, Biology and Medicine (Jun. 18, 2011) 7(5): 541-550).*
Taylor 2010 (Biochemistry (2010) 49: 3261-3272).*
International Search Report for PCT/GB2012/052513 mailed Apr. 4, 2013.
Li Ling Lee et al., "Discovery of Amyloid-Beta Aggregation Inhibitors Using en Engineered Assay for Intracellular Protein Folding and Solubility", Protein Science, vol. 18, No. 2, Feb. 1, 2009, pp. 277-28.
Ke-Jie Yin et al., "A [beta] 25-35 Alters AKt Activity, Resulting in BAD Translocation and Mitochondrial Dysfunction in Cerebrovascular Endothelial Cells", Journal of Cerebral Blood Flow & Metabolism, vol. 25, No. 11, Jun. 22, 2005, pp. 1445-1455.
Qu H Y et al., "Transducible P11-CNTF Rescues the learning and Memory Impairments Induced by Amyloid-Beta Peptide in Mice", European Journal of Pharmacology, vol. 594, No. 1-3, Oct. 10, 2008, pp. 93-100.
Lindsay M A, "Peptide-Mediated Cell Delivery: Aplication in Protein Target Validation", Current Opinion in Pharmacology, vol. 2, No. 5, Oct. 1, 2002, pp. 587-594.
Mark Taylor et al., "Effect of Curcumin-Associated and Lipid Ligand-Functionalized Nanoliposomes on Aggregation of the Alzheimer's A [beta] Peptide", Nanomedicine: Nanotechnology, Biology and Medicine, vol. 7, No. 5, Jun. 18, 2011, pp. 541-550.
Kumar et al, "Localization of antimicrobial peptides on polymerized liposomes leading to their enhanced efficacy against *Pseudomonas aeruginosa*", Mol Biosyst. Mar. 2011; 7(3):711-713.
Ono et al, "Curcumin Has Potent Anti-Amyloidogenic Effects for Alzheimer's β-Amyloid Fibrils In Vitro", Journal of Neuroscience Research 75:742-750 (2004).

* cited by examiner

*Primary Examiner* — Marcela M Cordero Garcia
*Assistant Examiner* — Mindy Newman
(74) *Attorney, Agent, or Firm* — Nixon & Vanderhye P.C.

(57) ABSTRACT

Compositions useful for the prevention and/or treatment of Alzheimer's disease are disclosed. The composition comprises carrier particles each linked to a plurality of peptide constructs comprising a peptide binding sequence capable of binding to an amyloid protein and a transit amino acid sequence linked to said binding sequence. The binding sequence may be retroinverted D-peptide mimetic of an L-peptide binding sequence and the transit sequence may be a D-peptide mimetic of an L-peptide transit sequence (e.g. TAT) The preferred peptide construct comprises the sequence rGffvlkGrrrrqrrkkrGy. The preferred carrier particles are liposomes.

21 Claims, 14 Drawing Sheets

EACH PINP COULD POTENTIALLY TRAP MANY Aβ MONOMERS AND OLIGOMERS

COMPOSITIONS FOR BINDING TO AMYLOID PROTEINS

This application is the U.S. national phase of International Application No. PCT/GB2012052513 filed 10 Oct. 2012 which designated the U.S. and claims priority to GB 1117439.8 filed 10 Oct. 2011, and GB 1202569.8 filed 15 Feb. 2012, the entire contents of each of which are hereby incorporated by reference.

The present invention relates to compositions which are comprised of therapeutically administrable carrier particles bonded to peptide constructs that are capable of binding to amyloid proteins and which are useful particularly, but by no means exclusively, for the prevention and/or treatment of neurodegenerative diseases characterised by the formation of extracellular amyloid deposits (e.g. senile plaques) and/or intracellular inclusion bodies containing protein fibrils. The invention has particular application to the prevention and/or treatment of Alzheimer's disease (AD). AD is the most common cause of dementia in the elderly population and is the fourth most common cause of death in Western countries after heart disease, cancer and stroke (1-3).

There is substantial well known evidence from molecular genetics, transgenic animal studies and aggregation/toxicity studies to suggest that the conversion of the β-amyloid (Aβ) peptide from monomers into aggregated forms in the brain is a key event in the pathogenesis of AD. The predominant and initial peptide deposited in senile plaques in the brain in AD is Aβ1-42 (42 amino acids in length) which is highly fibrillogenic (13-14). Another prominent feature of AD is the formation of neurofibrillary tangles (NFTs) inside nerve cells, which are derived from a highly phosphorylated form of tau protein. However, NFTs are likely to represent a secondary feature, following on from the deposition of Aβ. Many other neurodegenerative diseases (e.g. Parkinson's disease, motor neuron disease, frontotemporal dementia, Huntington's disease, the prion diseases) are also closely associated with the aggregation of different proteins in the brain. There are also many different types of amyloid disease where abnormal fibrillar protein deposits accumulate in wide variety of tissues and organs in the body, outside of the brain.

In the case of AD, it seems increasingly likely that early 'soluble oligomers' are responsible for the toxic effects of Aβ, rather than fully-formed amyloid fibres, and these small oligomers could be one of the major causes of neurodegeneration and memory loss in vivo (4-10). Inhibition of Aβ aggregation, especially in its early stages, is therefore a potential therapeutic target for AD (11-12). Likewise, the inhibition of early oligomer formation could also be a viable approach to the treatment of other amyloid diseases.

For completeness, we note that there is a second prominent form of β-amyloid, Aβ1-40, which has a shorter sequence of amino acids than Aβ1-42 and is less fibrillogenic. The aggregation of Aβ1-40 is, therefore, potentially easier to inhibit than that of Aβ1-42. The goal of clinicians is to have a treatment directed at the more fibrillogenic (and more neurodegenerative) Aβ1-42. Hereinafter, the abbreviation Aβ, when unqualified, means Aβ1-42.

Considerable progress has been made already in discovering inhibitors of Aβ1-40 and/or Aβ1-42 production or aggregation (15-16). One of the strategies employed has been the use of peptide-based inhibitors (17). These have been focused, generally, on the internal Aβ (15-22) sequence, QKLVFFAE (SEQ ID NO. 1) (see table below for a list of single letter codes as conventionally used for amino acids as used in the present specification), because this region has been reported to be primarily responsible for the self-association and aggregation of the Aβ peptide (18, 19).

| Abbreviation | Amino acid |
|---|---|
| A | Alanine |
| C | Cysteine |
| E | Glutamic Acid |
| F | Phenylalanine |
| G | Glycine |
| K | Lysine |
| L | Leucine |
| Q | Glutamine |
| R | Arginine |
| V | Valine |
| Y | Tyrosine |

For example, Soto and co-workers have designed 'β-sheet breaker peptides' by incorporating proline residues into part of this peptide sequence (20, 21) and other strategies have used N-methylated peptides (22, 23) or peptides linked to an oligolysine disrupting element (24). Some further modifications of these peptide inhibitors have included the incorporation of charged residues to aid solubility (25), the use of D-amino acids to improve stability (25, 26), and the attachment of targeting sequences to the peptides to enhance their cell and blood brain barrier permeability (25). However, we are not aware of any peptide-based inhibitors that have entered into human clinical trials.

A peptide-based inhibitor, named OR2, with the amino acid sequence RGKLVFFGR-NH$_2$ (SEQ ID NO. 2), was shown previously to inhibit Aβ oligomer and fibril formation (27) and a 'retro-inverted' version of this peptide (called RI-OR2) retained this activity (28). In the retro-inverted peptide, the natural L-amino acids are replaced by unnatural D-amino acids and the sequence is reversed (28). In surface plasmon resonance (SPR) experiments, OR-2 and RI-OR2 were shown to bind to immobilized Aβ1-42 monomers and fibrils, but with only modest affinity (dissociation constant (Kd) of 9-29 μM) (28). Moreover, these OR2 and RI-OR2 inhibitors were only effective at inhibiting Aβ aggregation at relatively high molar ratios of inhibitor: Aβ (5:1, 2:1, 1:1, 1:2, 1:5) and so cannot be considered as very potent inhibitors (27, 28).

It is an objective of the present invention to obviate or mitigate the above mentioned disadvantages.

According to a first aspect of the present invention there is provided a composition comprising therapeutically administrable carrier particles each linked to a plurality of peptide constructs comprising a peptide binding sequence capable of binding to an amyloid protein and a transit amino acid sequence linked to said binding sequence. Compositions in accordance with the first aspect of the invention have been found to be surprisingly effective at inhibiting or preventing the aggregation of amyloid proteins (or even effecting disaggregation of aggregated forms of amyloid proteins) and are, therefore, deemed useful for the prevention or treatment of diseases characterised by such aggregation. The finding that the compositions of the first aspect of the invention have these advantages is surprising for at least three reasons. Firstly, the free peptide constructs (in a form in which they are unattached to the carrier particles) which are comprised of a binding sequence and a transit amino acid sequence have, surprisingly, been found to have significantly enhanced binding affinity for amyloid proteins as compared to the binding sequence alone (i.e. not linked to the transit amino acid sequence). This finding alone is surprising and unexpected, because the transit sequence is designed only to improve cell or blood-brain barrier permeability and not to improve binding affinity. Secondly, although the free peptide construct per se has improved binding affinity for the amyloid protein (as compared to the binding sequence alone) it does not have an improved ability to prevent aggregation of the amyloid protein (as compared to the binding sequence alone). Nevertheless, when a plurality of the peptide constructs are attached, preferably covalently, to the carrier particles (e.g. such that there are at least 100 or, more usually, at least 1000 such sequences attached to each carrier particle) the resulting composition is remarkably effective at inhibiting or preventing aggregation of amyloid proteins (or even effecting disaggregation of aggregated forms of amyloid proteins). Thirdly, when a plurality of other types of aggregation inhibitors that are not the subject of the present invention, for example curcumin, a well known inhibitor of Aβ aggregation, are attached to carrier particles, they do not show the same dramatic increase in ability to prevent amyloid aggregation (or effect amyloid disaggregation) (30).

The invention is applicable particularly to neurodegenerative diseases that are characterised by aggregation of amyloid proteins, examples of which include Alzheimer's disease, Parkinson's disease, dementia with Lewy bodies, Huntington's disease, spinocerebellar ataxias, frontotemporal dementias, motor neuron disease (alternatively called amyotrophic lateral sclerosis) and prion diseases (e.g. Creutzfeld Jacob disease). The invention is however also applicable to non-neurodegenerative diseases in which there is aggregation of amyloid proteins, e.g. late-onset (type 2) diabetes mellitus.

The peptide constructs of the invention will usually be comprised of a maximum of 50 amino acid residues and generally significantly less, e.g. a maximum of 30 or 25. Usually the amino acid sequence involved in binding to the amyloid protein will be at the free end of the construct (i.e. at the end opposite to that by which the construct is linked, via the transit sequence, to the carrier particle). The transit amino acid sequence may be attached directly to the binding sequence but, if not, then there will generally be a maximum of 5 intermediate amino acid residues.

In preferred embodiments of the invention, the binding sequence and the transit amino acid sequence of the peptide construct comprise mainly or wholly of D-amino acids so that the construct as a whole is comprised mainly or wholly of such D-amino acids so as to resist degradation of the construct in vivo. In the following description, the convention is adopted that the corresponding L- and D-amino amino acids are represented by the same letter in upper and lower case, respectively (e.g. R for L-Arginine and r for D-Arginine). It will, however, be appreciated that the amino acid glycine does not exist in D- and L-forms and is therefore simply represented by the upper case letter G.

In preferred embodiments of the invention, the binding sequence in the peptide construct is a retroinverted D-peptide mimetic of an L-peptide sequence capable of binding to the amyloid protein. Similarly, it is preferred that the transit sequence in the peptide construct is a retroinverted D-peptide mimetic of an L-peptide transit sequence.

For AD, the peptide binding sequence in the peptide construct may be one that is capable of binding to Aβ1-42. More preferably, the binding sequence is one that is capable of binding to all or part of the internal sequence QKLVFFAE (SEQ ID NO. 1) (amino acid residues 15-22) of that peptide. In particularly preferred embodiments of the invention, the binding sequence in the peptide construct comprises a contiguous sequence of at least four, at least five, at least six or at least seven D-amino acids from the sequence eaffvlkq.

The binding sequence may also comprise the whole sequence eaffvlkq.

There are other suitable targets for the proteins implicated in the many other amyloid diseases. Examples include, but are not restricted to, residues 68-72 of α-synuclein=GAVVT (SEQ ID NO. 3) (33); residues 153-160 of the prion protein=NMHRYPNQ (SEQ ID NO. 4) (34); and residues 23-28 of amylin=FGAILS (SEQ ID NO. 5) (35). These are the amyloid proteins implicated, respectively, in Parkinson's diseases and related disorders, the prion diseases, and late-onset (type 2) diabetes mellitus.

The binding sequence may be associated with Gr residues at either or both ends (e.g. such a flanked sequence may comprise rGffvlkGr). The advantage of such an association is that it flanks the inhibitor sequence with one or two soluble amino acids (i.e. arginine='r') and makes the inhibitor more soluble and less likely to interact with itself. The glycine ('G') makes the amino acid chain very flexible at that point, so that the inhibitor sequence can still interact with its target sequence on the amyloid molecule.

The transit sequence in the peptide construct of the invention is one capable of transporting the binding sequence into cells or across the blood-brain barrier. The transit sequence may be a retroinverted D-peptide mimetic of an L-peptide transit sequence. Such L-peptide transit sequences are known in the art and include the TAT peptide, i.e. YGRKKRRQRRR (SEQ ID NO. 6). Other transit sequences are known and include but are not restricted to flock house virus (FHV) coat-(35-49), *Drosophila* Antennapedia-(43-58) and basic peptides such as octa and hexa arginine peptides. The presence of the transit amino acid sequence not only provides the surprising effect of enhancing the binding of the inhibitor sequence to the amyloid protein but also serves to ensure that the carrier particles and associated peptide constructs can pass into the brain and/or across cell membranes. It will be appreciated that, in the case of AD and other neurodegenerative diseases, the particles must be able to pass into the brain, because this is the site of protein aggregation. Also, it may be necessary to locate the peptide constructs intracellularly if (as is the case with many, but not all, amyloid diseases) this is the site of amyloid aggregation or inclusion body formation.

It is particularly preferred that the transit sequence for the peptide construct is rrrqrrkkrGy, i.e. the retroinverted D-peptide mimetic of the TAT peptide.

Preferred peptide constructs for use in the invention for the treatment of AD comprise the sequence:

RGffvlkGrrrrqrrkkrGy wherein the underlined portion is the binding sequence and the italicised portion is the transit amino acid sequence, there being flanking Gr residues on either side of the binding sequence, as shown.

The preferred peptide construct identified above may be synthesised using standard peptide chemical routes to produce a molecule of the formula:

Ac-rGffvlkGrrrrqrrkkrGy-$NH_2$ which is designated herein as RI-OR2-TAT and which may be coupled to carrier particles by standard chemical routes, e.g. as exemplified below. One method for coupling the RI-OR2-TAT to the carrier particles involves the attachment of an additional cysteine residue to the amino acid sequence, as follows, so that the peptide can be coupled to the particles via the sulphydryl group on the cysteine.

Ac-rGffvlkGrrrrqrrkkrGyc

As discussed above, compositions in accordance with the invention comprise peptide sequences (discussed more fully above) linked to carrier particles. The carrier particles will, for preference, have a maximum size of 200 nm and/or may be more broadly be classed as nanoparticles. The carrier particles are preferably liposomes. For the purposes of the present invention, liposomes may be produced by extruding a suspension of mixed lipids through a small particle filter and then selecting for correct size range using an appropriately sized filter. Attachment of the peptide constructs to the liposomes may be via "click" chemistry (see reference 30), e.g. using linking groups. One example of such a linking group is maleimide which allows the direct attachment of the peptide constructs to the liposomes and is preferably included as about 2.5% of the total lipid concentration.

The following equation schematically illustrates the linking of the preferred peptide construct to a liposome using a maleimide linker, via an additional cysteine amino acid:

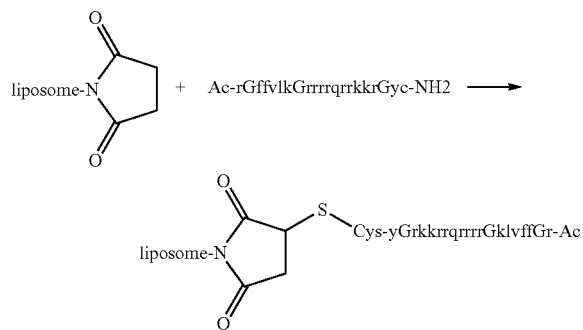

Our findings have demonstrated (see Examples below) that RI-OR2-TAT gives a large (approximately 1000-fold) increase in the affinity of the binding of the inhibitor to Aβ fibrils (giving a Kd value in the order of 41-75 nM) as compared to the molecule Ac-rGffvlkGr-NH$_2$ (which we designate herein as RI-OR2), i.e. a molecule comprising the binding sequence of RI-OR2-TAT but not the transit amino acid sequence. Moreover, covalent attachment of RI-OR2-TAT to nanoliposomes (cholesterol:sphingomyelin [1:1] with 2.5% maleimide) resulted in a further increase in this binding affinity (Kd) to 14-44 nM. TAT-RI-OR2 when attached to liposomes proved to be an extremely effective inhibitor of Aβ aggregation and was able to block the formation of Aβ oligomers and fibrils even at a 1:500 molar ratio of total lipids:Aβ. The peptide (i.e. RI-OR2-TAT) attached to the liposomes is present at only 2.5% of this amount, and so at a 1:500 molar ratio of total lipids:Aβ there is a molar ratio of 1:20,000 of the inhibitory peptide:Aβ. These modified inhibitors, which are referred to here as PINPs (Peptide Inhibitor NanoParticles), are remarkably effective inhibitors of Aβ aggregation and will, therefore, be viable drugs for the treatment of AD and related conditions because of their potent ability to stop the assembly of Aβ into toxic oligomers in the brain.

Compositions in accordance with the invention are useful for the prevention and/or treatment of neurodegenerative diseases. For this purpose, the carrier particles will generally be associated with a pharmaceutically acceptable vehicle to facilitate administration of the composition to a patient. Depending on the intended mode of administration and nature of the carrier particles, the pharmaceutically acceptable vehicle may be a liquid or a solid. In the case of preferred compositions based on liposomes as carrier particles, these may be produced (and derivatized with the peptide constructs) in the form of an aqueous dispersion.

Compositions in accordance with the invention may be administered by an oral, intravenous, intranasal (including nasal spray), epidural, subcutaneous, intramuscular or pulmonary (inhalation) route. Typically, from 1 mg to 100 mg of peptide construct attached to the carrier particles may be administered per day. Administration in these amounts may be everyday or periodically, e.g. one to three times per week. Therapeutic use of the composition is preferably commenced prior to a patient developing the symptoms of the appropriate amyloid or neurodegenerative disease (e.g. for Alzheimer's disease, during the stage known as "mild-cognitive impairment"). Therapeutic use may be maintained for as long as a patient is a risk of developing, or suffering from, the relevant amyloid or neurodegenerative disease.

In addition to their therapeutic applications, compositions in accordance with the invention may be used in diagnostic applications for the sensitive detection of amyloid deposits (by brain imaging techniques) in living human patients. For this purpose, the carrier particles themselves or the peptide constructs may be derivatised (either before or after attachment of the constructs to the carrier particles) with fluorescent or radioactive imaging modalities that will allow the particles to be administered to patients by the same routes as set out above for therapeutic administration and detected (e.g. imaged) by techniques well known in the art. Thus, for example, the carrier particles with attached peptide constructs could be derivatised with Technetium-99m (T99m) or Iodine-123 (I-123), both of which can be used as radioactive tracers in medical scanning equipment.

It is also envisaged that the peptide constructs per se, with their enhanced ability to bind to amyloid proteins, will also be useful in diagnostic applications, e.g. in vitro or in vivo. In the foregoing description, various specific sequences have been described for the binding sequences, transit amino acid sequences and peptide constructs. It will however be appreciated that any derivatives or analogues of each and every constituent part of the complete peptide component of the invention are also effective for inhibiting and/or reversing the aggregation of the amyloid proteins concerned. These could be derivatives or analogues of the sequence involved in the binding with the amyloid protein (e.g. residues 16-20 of Aβ=KLVFF (SEQ ID NO. 7); residues 68-72 of α-synuclein=GAVVT (SEQ ID NO. 3) (33); residues 153-160 of the prion protein=NMHRYPNQ (SEQ ID NO. 4) (34); residues 23-28 of amylin=FGAILS (SEQ ID NO. 5) (35), the solubilizing residues immediately flanking this sequence (e.g. rG . . . Gr), or the transit peptide sequence (e.g. the TAT peptide), which, according to a preferred embodiment of our invention, are all retro-inverted. These derivatives or analogues may include, for example, simple amino acid substitutions, where one amino acid residue is replaced by another amino acid with similar characteristics (e.g. replacement of glycine with alanine, which are both simple uncharged amino acids; or replacement of the positively charged lysine with arginine, another positively charged amino acid). They may also include N-methylated derivatives of the peptides, where some or all of the amino acids in the sequence are replaced by N-methylated amino acid residues. They may also include peptoid derivatives, where the position of the side chain is shifted from the α-carbon atom to the nitrogen atom [Additional Ref. 1]. Peptoid derivatives of the peptides of the invention may be readily designed from knowledge of the structure of the chosen peptide, using, for example, commercially available software designed for this purpose.

BRIEF DESCRIPTION OF THE DRAWINGS

The invention will be further described with reference to the following non-limiting Examples for which procedures are described in the Appendix to this specification and the accompanying drawings, in which.

EXAMPLE 1

Figure 1:
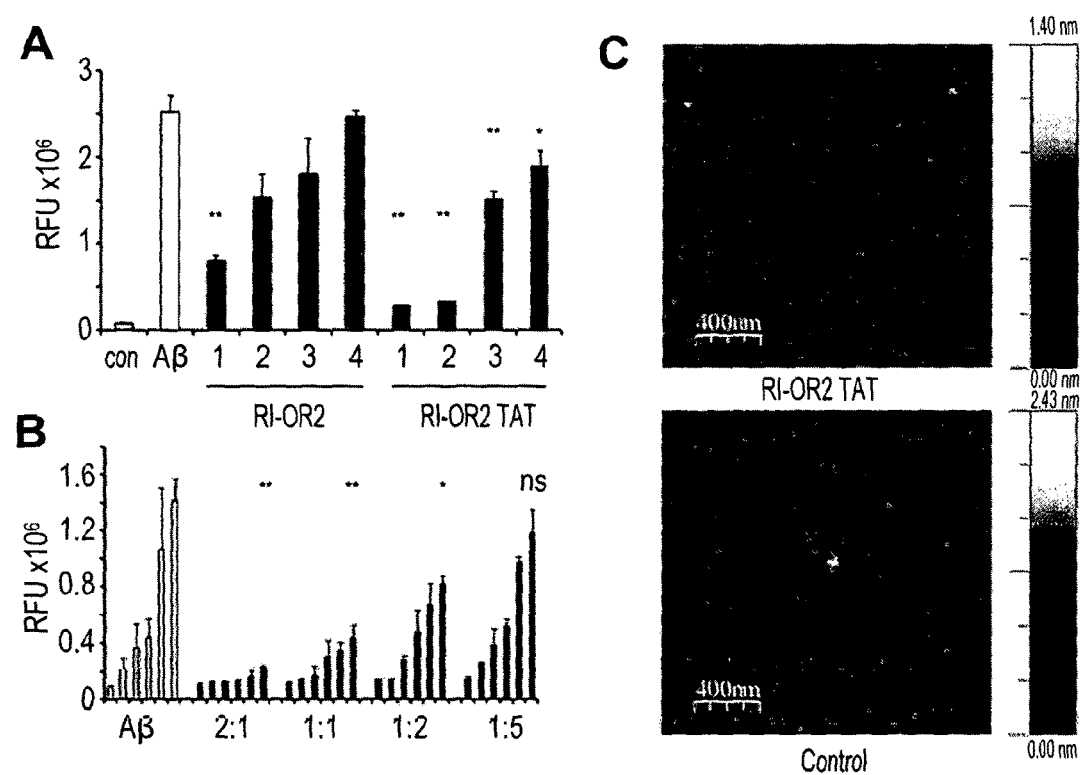
FIGS. 1A-C show that RI-OR2 and RI-OR2-TAT inhibit the aggregation of Aβ42.

This Example demonstrates the ability of RI-OR2-TAT to inhibit the formulation of Aβ42 oligomers and fibrils in vitro.

Three techniques were used for the purpose of this Example, namely (i) Thioflavin T (ThT) assay for Aβ fibrils (Appendix, Section 2), (ii) Immunoassay for Aβ oligomers (Appendix, Section 3), and (iii) Atomic Force Microscopy (Appendix, Section 6).

The results are shown in FIGS. 1A, 1B and 1C.

FIG. 1A shows ThT data for Aβ42 incubated with and without RI-OR2 and RI-OR2-TAT: 'con' is buffer only; 'Aβ' is Aβ42 incubated at 25 µM for 48 h, with no inhibitor; the dark grey bars are Aβ42 incubated for 48 h with RI-OR2 at 1—1:1, 2—1:2, 3—1:4, 4—1:10 molar ratios of inhibitor:Aβ; and the black bars are Aβ42 incubated with RI-OR2-TAT at these same molar ratios. FIG. 1B shows effects of the inhibitors on detection of multimeric Aβ42 by immunoassay. The data for Aβ42 alone, incubated at 12.5 µM, are shown on the left (pale bars), and for Aβ42 incubated with 2:1, 1:1, 1:2 and 1:5 molar ratios of RI-OR2-TAT:Aβ on the right (black bars). In each case, the consecutive bars are for 0, 4, 8, 24 and 48 h incubations. For both (A) and (B), *denotes $p<0.05$ for treated sample versus untreated control, and **denotes $p<0.01$. (c) AFM images obtained from Aβ42 incubated at 25 µM for 24 h in the presence (RI-OR2-TAT) or absence (control) of a 1:2 molar ratio RI-OR2-TAT:Aβ. (C) AFM images of a 24 h incubation of Aβ42 (25 µM) in the presence and absence (Control) of RI-OR2-TAT (12.5 µM). Scale bar is to the right.

In the thioflavin T (ThT) assay, which detects mainly amyloid fibrils, the presence of RI-OR2-TAT resulted in lower fluorescence after 48 h incubation of Aβ42 at molar ratios of 1:1, 1:2, 1:4 and 1:10 (inhibitor:Aβ42) and seemed to be a slightly better inhibitor than RI-OR2 (FIG. 1A). These inhibitors were also tested in an immunoassay technique for the detection of early-stage Aβ oligomers [28]. This assay uses monoclonal anti-Aβ antibody 6E10 to capture Aβ from solution and a biotinylated form of 6E10 as the detection antibody, in a sandwich system. Monomeric Aβ has only a single 6E10 epitope, which is occupied by the capture antibody, and so it cannot subsequently bind to the detection antibody. On the other hand, multimeric Aβ has binding sites available for both capture and detection, giving rise to a strong immunoassay signal. In Aβ aggregation time-course experiments, this assay produces a signal before the ThT method, when only small oligomers are present [28]. RI-OR2-TAT considerably reduced the development of an immunoassay signal, at 2:1 and 1:1 molar ratios of inhibitor:Aβ42, even at the earliest time points where such a signal was detectable (4 and 8 h), indicating inhibition of oligomer formation (FIG. 1B). This was confirmed by atomic force microscope (AFM) images (FIG. 1C), which showed clear inhibition of oligomer formation at a 1:2 molar ratio of RI-OR2-TAT:Aβ42.

EXAMPLE 2

This Example demonstrates the relative binding affinities of RI-OR2-TAT and RI-OR2 for Aβ2.

The procedure of this Example was conducted using Surface Plasmon Resonance in accordance with Section 5 of the Appendix.

Figure 2:
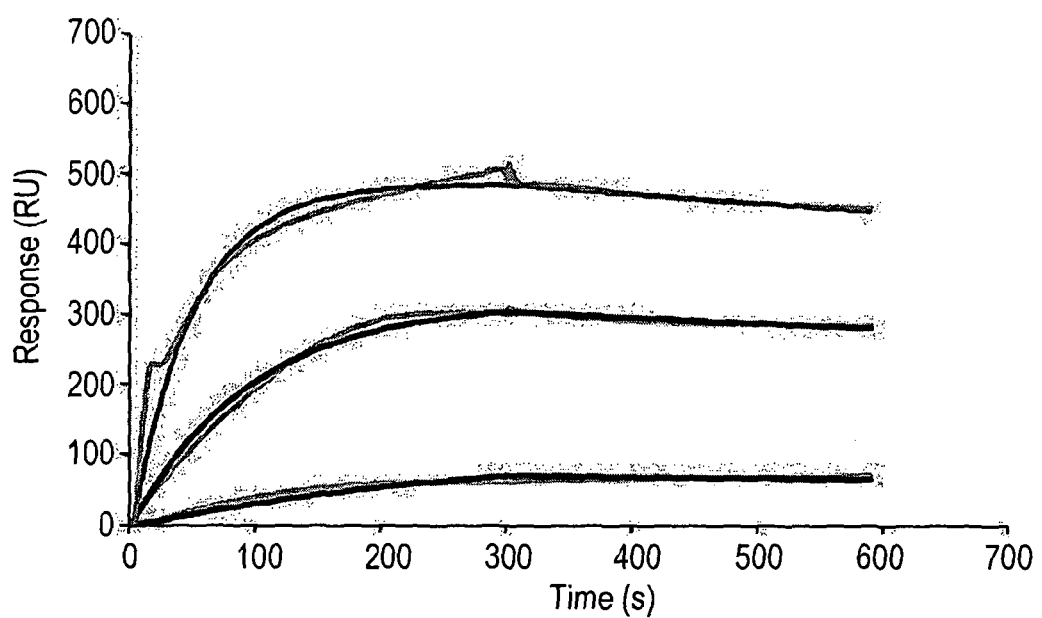
FIG. 2 shows binding of RI-OR2-TAT to immobilized Aβ42 fibrils, as shown by surface plasmon resonance (SPR) spectroscopy.

The results are shown in FIG. 2. In this Fig., the upper line shows data for 6 µM RI-OR2-TAT, the middle line for 3 µM RI-OR2-TAT and the lower line for 1 µM RI-OR2-TAT. The non-specific binding obtained from the reference surface has been automatically subtracted from all data. Fitted curves are shown in black.

The results of this Example demonstrate that RI-OR2-TAT bound to immobilized Aβ in a concentration-dependent manner, when surface plasmon resonance (SPR) spectroscopy was used to estimate the binding constant between this inhibitor and fibrils derived from Aβ42 (FIG. 2). The binding was characterized by a fast association rate and a slow dissociation rate, with $K_{on}$ values of $3680\pm615$ $M^{-1}$ $s^{-1}$ and $K_{off}$ values of $3.7\pm1.5\times10^{-4}$ $s^{-1}$, respectively. The curves were fitted separately using the simplest Langmuir 1:1 interaction model, and the calculated apparent affinity value $(K_d)$ was 58-125 nM. This range of values represents a binding affinity of RI-OR2-TAT for Aβ42 fibrils that is ~100-fold higher than the previously reported value of $K_d$ related to the binding of RI-OR2 to Aβ42 fibrils ($K_d$=9.5 µM) (28).

EXAMPLE 3

This Example demonstrates that RI-OR2-TAT inhibits the toxic effects of Aβ42 ON CELLS.

This Example was carried out in accordance with the procedure described in Section 4 of the Appendix ("Cell Penetration and Cytotoxicity Experiments") to the extent that it relates to Example 3 and the results are shown in FIGS. 3A and 3B. In FIG. 3A, the black bars show data for the viability of SHSY-5Y neuroblastoma cells, as measured by LDH assay, following exposure to 12.5, 25, 50, 100 and 200 µM RI-OR2-TAT alone for 24 h. The light grey 'Con' bar shows data for cells maintained under the same conditions, but without RI-OR2-TAT, and the dark grey bar shows data for lysed cells. FIG. 3B shows the ability of RI-OR2-TAT to protect against Aβ42-mediated toxicity. The black bars are LDH assay data for cells grown in the presence of 5 µM Aβ42 plus 0.1, 0.5, 1, 5 or 10 µM RI-OR2-TAT for 24 h. The 'Aβ' bar shows data for cells grown in the presence of Aβ42 alone and the bars labelled 'Con' and 'Lysed cells' are the same as for (A). For both (A) and (B) *indicates p<0.05.

EXAMPLE 4

This Example demonstrates that (i) RI-OR2-TAT enters cultured cells, and (ii) crosses the blood brain barrier of APP/PS1 transgenic mice.

The procedure used for demonstrating that RI-OR2-TAT enters cultured cells is as described in Section 4 of the Appendix, to the extent that it relates to Example 4.

The procedure used for demonstrating that RI-OR2-TAT crosses the blood brain barrier of APP/TS1 transgenic mice is as described in Sections 6 to 8 of the Appendix to the extent they relate to Example 4.

Figure 4:
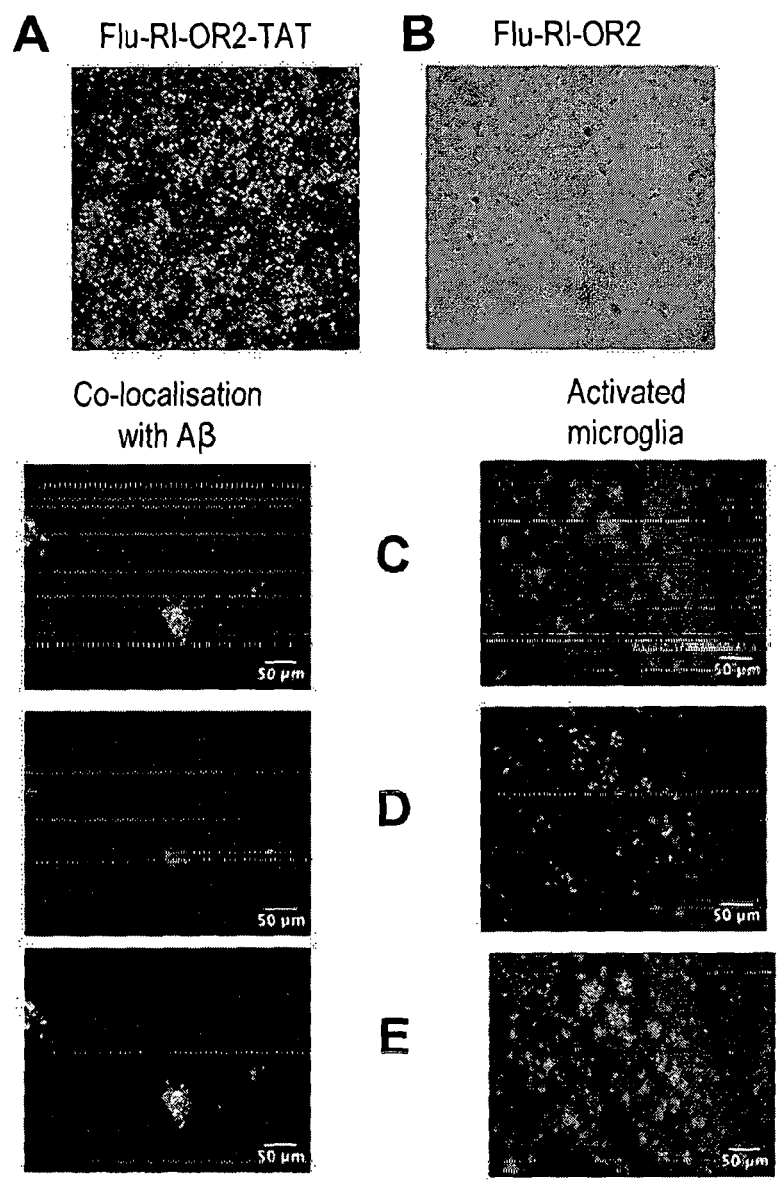
FIGS. 4A-E show that Flu-RI-OR2-TAT enters cultured SHSY-5Y cells and crosses the blood brain barrier of APP/PS1 transgenic mice.

Results are shown in FIGS. 4A-E. FIG. 4A shows a fluorescent microscope image of SHSY-5Y cells exposed to 1 µM RI-OR2-TAT for 10 mins. FIG. 4B is a corresponding image for cells exposed to Flu-RI-OR2, also at 1 µM, but for 1 h. FIG. 4C shows fluorescence images showing the detection of Flu-RI-OR2-TAT in sections of brain tissue following i.p. injection in 17-month old APP/PS1 transgenic mice. FIG. 4D shows the same sections as in FIG. 4C but with detection using AlexaFluor 555 labelled antibody against either (on the left) Aβ or (on the right) activated microglia/Iba 1. FIG. 4E shows merged images of FIGS. 4C and 4D above. Flu-RI-OR2-TAT is seen to be co-localised with Aβ and with activated microglial cells.

Fluorescent and light microscope images of SHSY-5Y cells exposed to 1 µM Flu-RI-OR2-TAT for 10 mins showed the build up of fluorescence inside the cells (FIG. 4A), whereas the fluorescence associated with Flu-RI-OR2 remained in the culture medium (FIG. 4B). Flu-RI-OR2-TAT was detected in sections of brain tissue following intraperitoneal (i.p.) injection in 17-month old APP/PS1 transgenic mice, demonstrating that it can cross the BBB. In a double labelling study, using AlexaFluor 555 labelled antibody against either Aβ or activated microglia/Iba 1, Flu-RI-OR2-TAT was found to be co-localised with amyloid plaques present in the cerebral cortex, and was also found inside activated microglial cells (FIGS. 4C, D, E).

EXAMPLE 5

This Example provides in vivo data in a mouse model for the peptide construct RI-OR2-TAT. Experimental results were provided by Professor Christian Holscher at Ulster University in their Alzheimer's mouse model (APP/presenilin).

This Example demonstrates that:
(i) RI-OR2-TAT decreases brain oligomer levels and amyloid plaque load in APP/PS1 transgenic mice; and
(ii) RI-OR2-TAT reduces the brain load of microglia and oxidative damage and stimulates neurogensis in APP/PS1 transgenic mice.

The procedure used was as described in Section 6-8 of the Appendix to the extent they relate to Example 5.

Results in respect of (i) are shown in FIGS. 5A-D which show representative images show amyloid deposits in the cortex region of 10 months old APP/PS1 mouse brains as shown by β-amyloid immunostaining in animals treated with (A) 0.9% saline or (B) 100 nmol/Kg RI-OR2-TAT in 0.9% saline. Scale bar=880 µm. (C) Quantitative analysis shows a decrease in mean plaque load in the cortex of APP/PS1 mice treated with RI-OR2-TAT compared to animals treated with saline. (D) Levels of soluble AB oligomers in these brains. Values represent mean±SEM of 4 animals per group, where * p<0.0001;  p<0.01, unpaired Student t-test.

Figure 5:
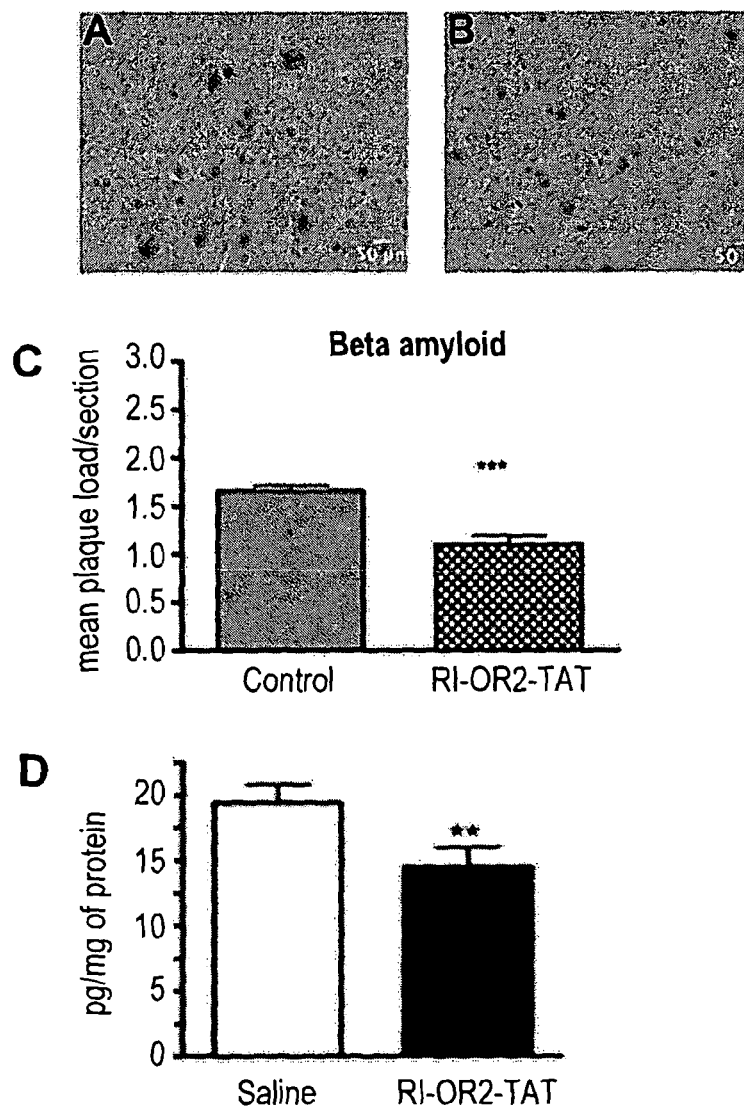
FIGS. 5A-D show that RI-OR2-TAT reduces the β-amyloid plaque load and levels of Aβ soluble oligomers in the brains of APP/PS1 transgenic mice.

As shown in FIG. 5 (A, B, C), treatment with 100 nMol/kg RI-OR2-TAT over a period of 21 days reduced amyloid plaque load by 32% in the cortex region of 10 months old APP/PS1 mouse brains, compared to animals treated with saline, as detected by β-amyloid immunostaining (p<0.0001, unpaired Student t-test, N=4 animals per group). Soluble Aβ oligomer levels in the brain, as detected by sandwich ELISA, were also reduced, by 25% (p<0.01, unpaired Student t-test) (see FIG. 5D).

The results in respect of (ii) are shown in FIGS. 6A-I which show representative images of activated microglia in the cortical region of APP/PS1 mouse brains as shown by Iba1 immunostaining in animals treated with (A) 0.9% saline or (B) 100 nmol/Kg RI-OR2-TAT in 0.9% saline; (C) quantitative analysis shows a decrease in mean microglial load in APP/PS1 mice treated with RI-OR2-TAT; detection of 8 oxo-guanine in the brains of animals treated with (D) 0.9% saline or (E) 100 nmol/Kg RI-OR2-TAT; (F) quantitative analysis shows a decrease in mean 8 oxo-guanine staining in APP/PS1 mice treated with RI-OR2-TAT; detection of immature neurons as stained for doublecortin in the dentate gyrus of APP/PS1 mice treated with (G) 0.9% saline or (H) 100 nmol/Kg RI-OR2-TAT; (I) quantitative analysis shows an increase in mean doublecortin staining in APP/PS1 mice treated with RI-OR2-TAT. Scale bar=880 µm. Values represent mean±SEM of 4 animals per group, where *** p<0.0001, unpaired Student t-test.

Figure 6:
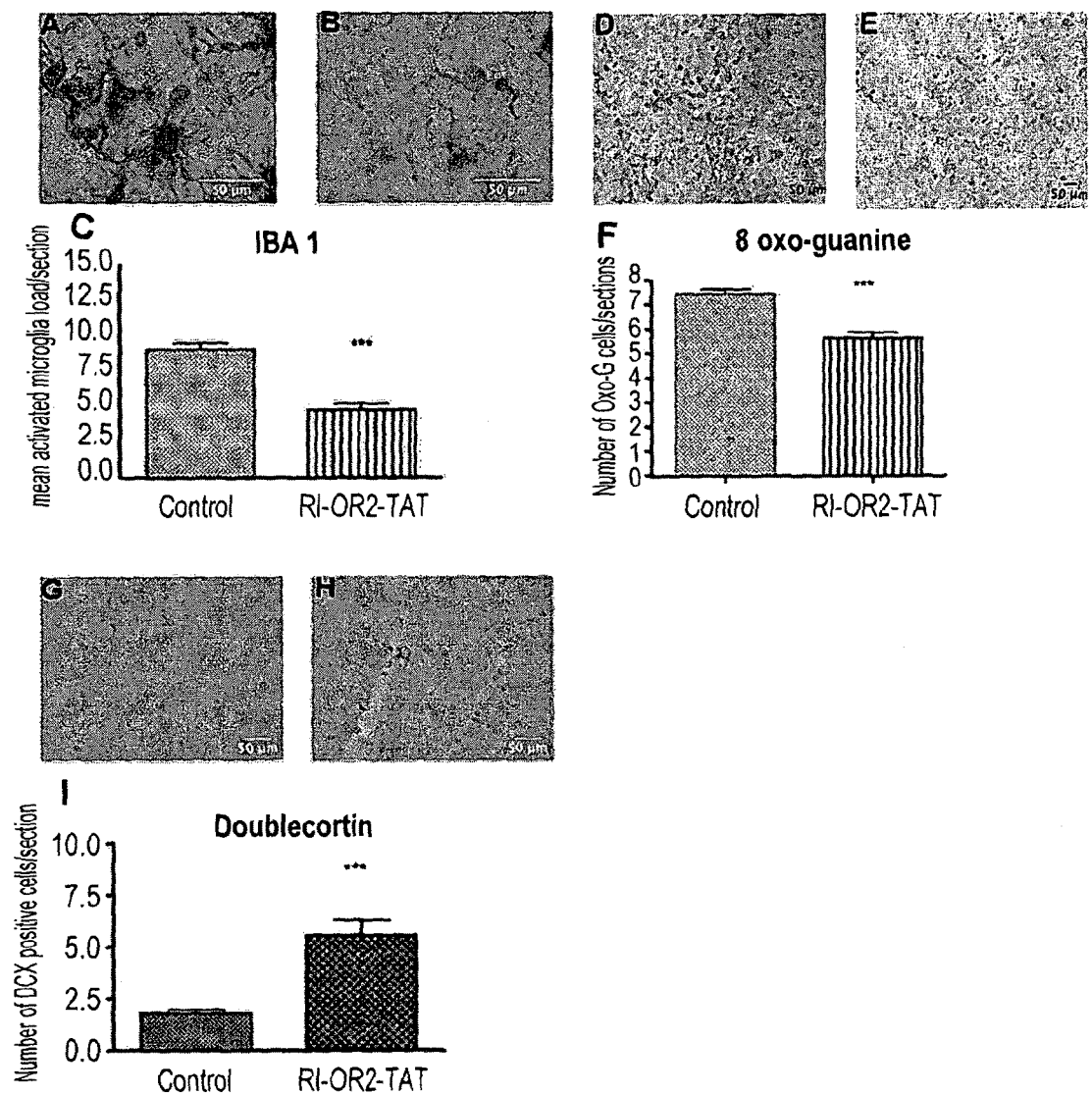
FIGS. 6A-I show that RI-OR2-TAT reduces the brain load of microglia and oxidative damage and stimulates neurogenesis in APP/PS1 transgenic mice.

As shown in FIG. 6, treatment with RI-OR2-TAT reduced the number of activated microglia in the cortex of APP/PS1 mouse brains of 10 months of age by 44% as shown by Iba1 immunostaining (p<0.0001, unpaired Student t-test) (FIG. 6A, B, C). This treatment also reduced the cortical level of 8-oxo-guanine immunostaining by 25% (p<0.0001, unpaired Student t-test) (see FIG. 6D, E, F) and increased the mean number of young doublecortin-expressing neurons in the dentate region by 210% (p<0.0001, unpaired Student t-test) (see FIG. 6G, H, I).

EXAMPLE 6

This Example demonstrates that PINPs have an average diameter of 130 nm, as determined by using Nanoparticle Tracking Analysis (using a Nanosight Instrument). The procedure described in Section 12 of the Appendix was used to prepare liposomes having attached thereto peptide constructs of the formula RI-OR2-TAT. Liposomes were obtained from Dr Maria Gregori and SPR data from Dr. Elisa Salvati at the University of Milano-Bicocca, Milan, Italy.

Figure 7:
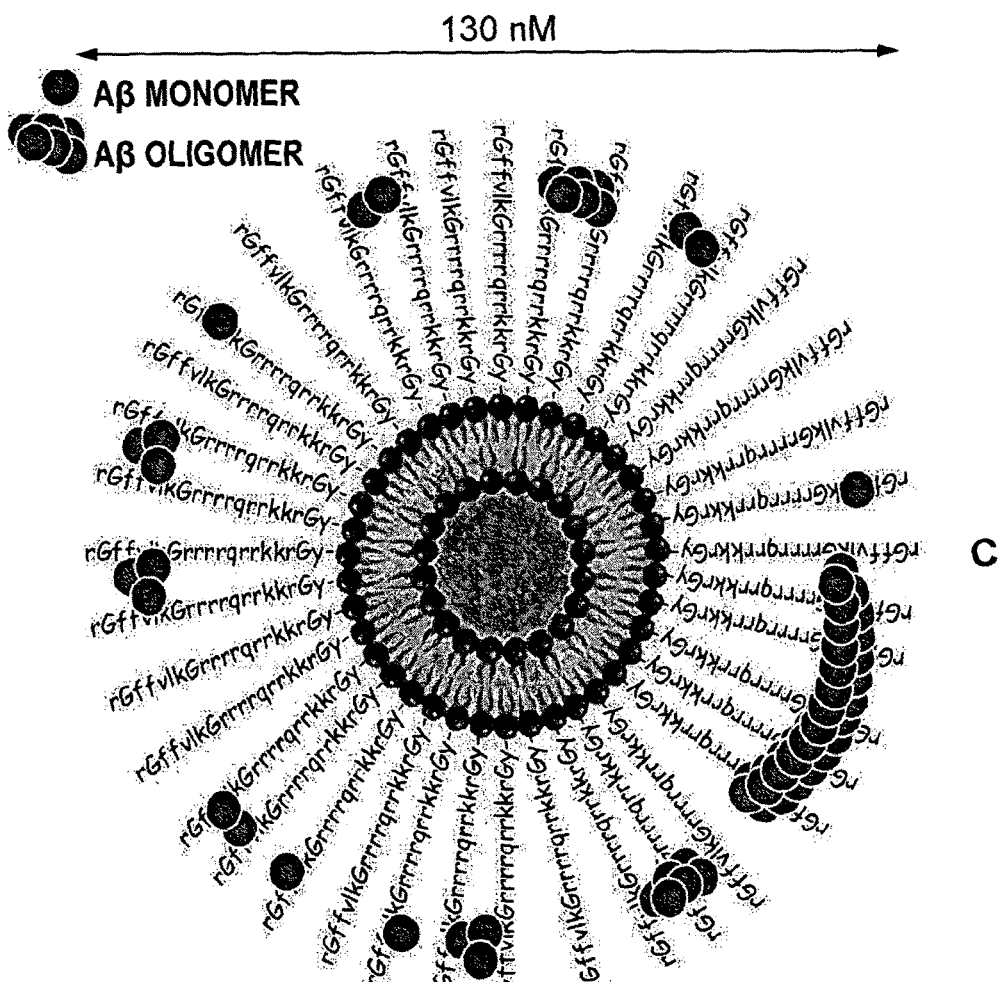
FIGS. 7 (a)-(c) show results for NTA analysis of PINPs derivatized with RI-OR2-TAT.

The particles were investigated by Nanoparticle Tracking Analysis (NTA) which is a method for visualizing and analyzing particles in liquids that can be used to determine the size of individual particles by tracking their rate of Brownian motion. The results are shown in FIGS. 7(a) and 7(b) in which:

FIG. 7(a) is an NTA analysis of PINPs (derivatized with RI-OR2-TAT) and reveals an average size (diameter) for these nanoparticles of 130 nm; and FIG. 7(b) is a still from part of a video frame taken from this same NTA analysis reveals three individual PINPs;

The schematic illustration of FIG. 1(c) shows that, based on their size, each of these PINPs should be able to interact with many Aβ monomers and/or oligomers.

EXAMPLE 7

This Example demonstrates that Surface Plasmon Resonance (SPR) studies show an unexpectedly high affinity for the binding of both RI-OR2-TAT and PINPs (derivatized with RI-OR2-TAT) to Aβ fibrils.

Figure 8:
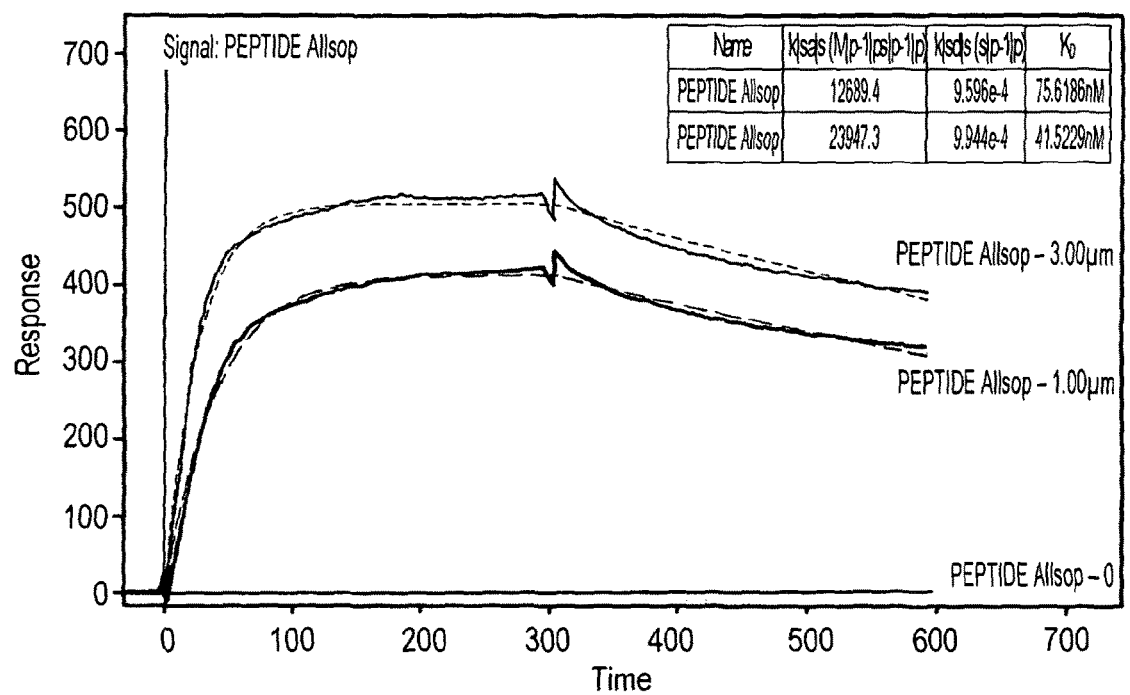
FIG. 8 shows the results of Surface Plasmon Resonance (SPR) studies for the binding of RI-OR2-TAT.
Figure 9:
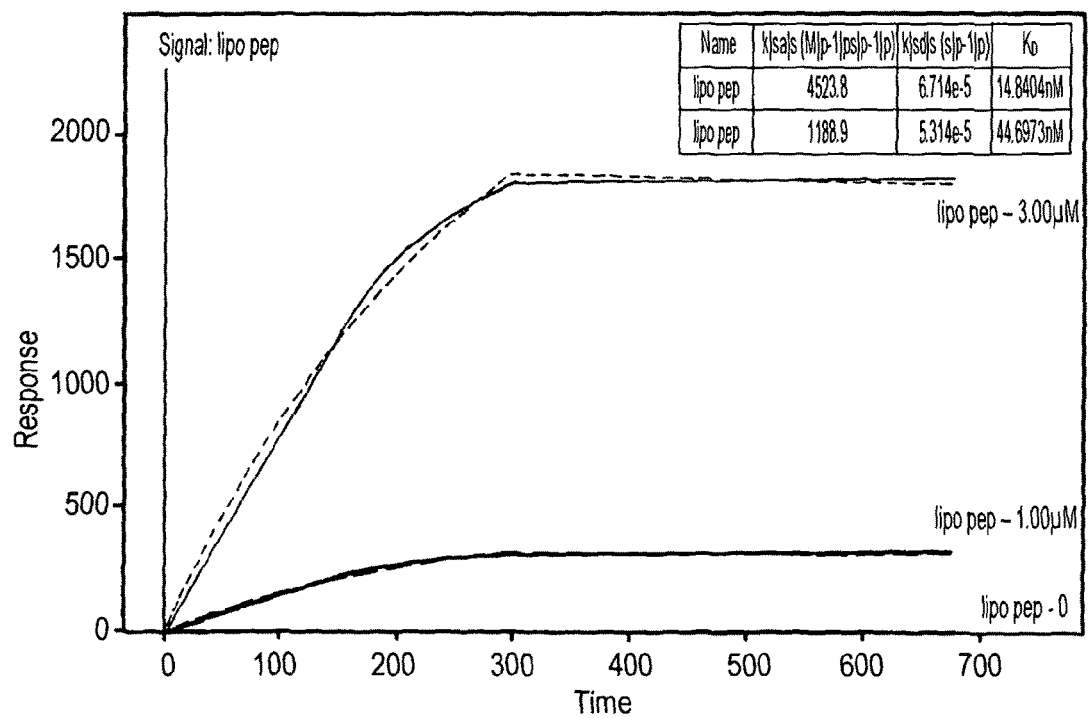
FIG. 9 shows the result of Surface Plasmon Resonance (SPR) studies for the binding of PINPs derivatized with RI-OR2-TAT to Aβ fibrils.

The results of these studies which were carried out as described in Section 14 of the Appendix are shown in FIG. 8 (for RI-OR2-TAT and FIG. 9 for PINPNS (derivatised with RI-OR2-TAT)).

SPR (Surface Plasmon Resonance) is a technique that can be used to measure the affinity of a substance for a substrate. The substrate (in this case Aβ fibrils) is bound to a solid surface and excited using a laser light source. The compound to be tested (e.g. PINPs) is allowed to flow over the bound substrate in suspension/solution and the emission spectra of the substrate will change if the compound binds. A second solution, without the test compound, can then added to elute any bound compound and the emission spectra may be observed to note loss of bound compound from the substrate. For a specific example regarding peptide binding to Aβ see reference (30).

In the examples presented here, The substance is introduced at a flow rate of 30 uL/min for 5 minute over the immobilized substrate. There is a spike in the signal which is due to the introduction of solvent without PINPs to show removal of the peptide bound to the Aβ fibrils. There are two plots related to addition of peptide at two different concentrations, 1 and 3 μM, plus a computer generated fitted curve for each one.

These SPR data can be interpreted to provide an estimate for the affinity of binding of the inhibitors to Aβ fibrils (28).

They reveal an unexpectedly high affinity, with a Kd of 15-75 nM, for the binding of both RI-OR2-TAT and PINPS (RI-OR2-TAT attached to liposomes) to Aβ fibrils. Published SPR data (28) on RI-OR2 (without TAT) have provided a binding affinity (Kd) for interaction with Aβ monomers and fibrils of 25-30 μM. Therefore the RI-OR2-TAT peptide shows approximately 1000 times greater binding affinity than without TAT, which was highly unanticipated because the additional TAT sequence is primarily designed to facilitate cell and blood brain barrier penetration, and not an increase in binding affinity.

EXAMPLE 8

This Example shows the results of a Thioflavin T assay showing demonstrating the ability of PINPs (derivatized with RI-OR2-TAT), to inhibit Aβ aggregation.

This Example was carried out using the procedure described in Section 2 of the Appendix. The results are shown in FIG. 10.

Figure 10:
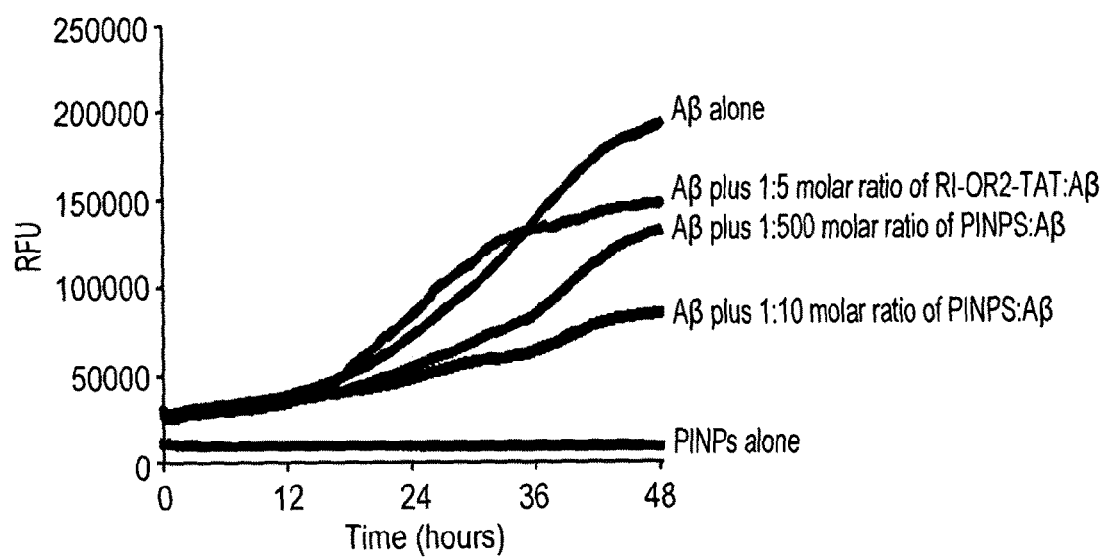
FIG. 10 illustrates the results of a Thioflavin T assay showing the ability of PINPs derivatized with RI-OR2-TAT to inhibit Aβ aggregation.

FIG. 10 shows data from an Aβ1-42 aggregation assay as measured by thioflavin T fluorescence. It can be seen that by 48 hours the fluorescent signal (RFU, relative fluorescence units) from Aβ alone has increased, indicating its aggregation into amyloid fibres. By 48 hours, the signal for Aβ1-42 treated with a 1:500 molar ratio of PINPs:Aβ is below that of Aβ1-42 alone, and even below that of Aβ1-42 treated with a 1:5 molar ratio of the unattached inhibitory peptide (i.e. RI-OR2-TAT):Aβ. This indicates that when this inhibitory peptide is attached to liposomes (i.e. in the form of PINPS) there is a remarkable increase in the potency of its ability to inhibit Aβ aggregation. Note that the inhibition of Aβ aggregation is more pronounced with a molar ratio of 1:10 PINPS:Aβ. For PINPS, the ratios mentioned above refer to total lipids:Aβ, whereas peptide:Aβ is only 2.5% of this amount. In the example above, this would mean at a 1:500 molar ratio of total lipids:Aβ there is a molar ratio of 1:20,000 of the inhibitory RI-OR2-TAT peptide:Aβ.

EXAMPLE 9

This Example demonstrates concentration-dependent inhibition of PINPs (derivatized with RI-OR2-TAT) on Aβ1-42 aggregation as assessed by thioflavin T assay. The results of this Example are shown in FIG. 11.

Figure 11:
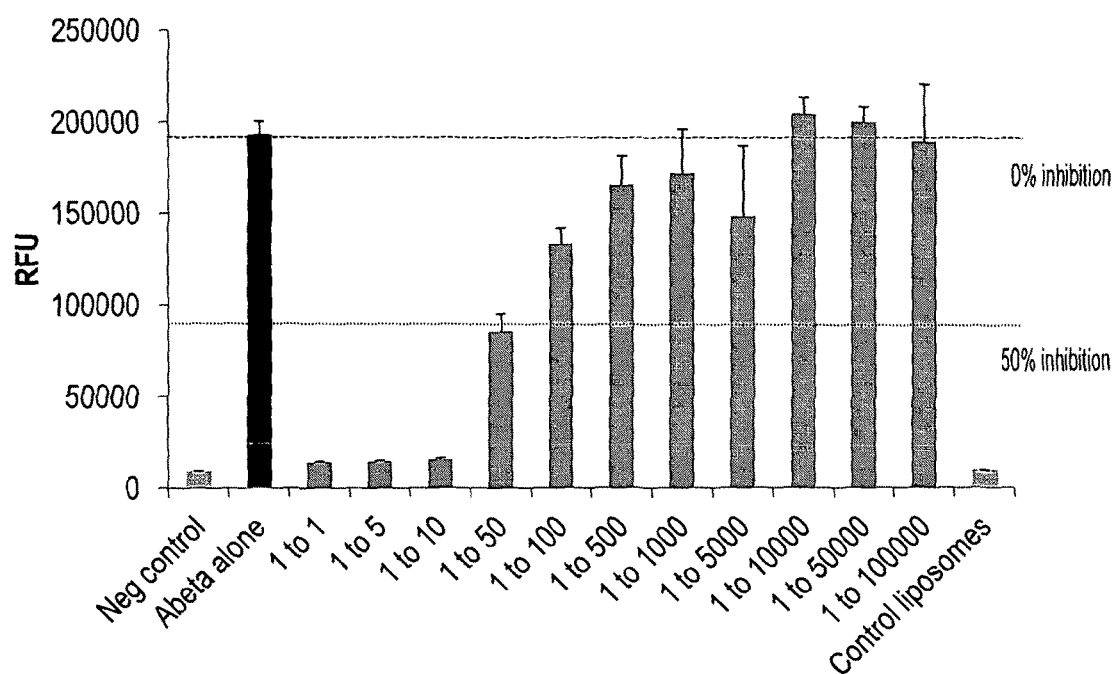
FIG. 11 shows concentration-dependent inhibition of PINPs derivatized with RI-OR2-TAT on Aβ 1-42 aggregation as assessed by Thioflavin T assay.

FIG. 11 (data in Table 1 below) shows the fluorescence data (RFU=relative fluorescence units) using a thioflavin T assay after 48 hours incubation of Aβ1-42 (at 25 μM) with various concentrations of PINPS. The data were obtained in the same type of experiment as that shown in Example 7. On the far left is a negative (Neg) control with no Aβ, showing background fluorescence only. Next is Aβ1-42 alone, which shows a substantial increase in fluorescence, indicative of amyloid fibril formation. This is followed by data for Aβ1-42 incubated with various molar ratios of PINPS (total lipids):Aβ from 1:1 to 1:100,000, followed by another control (last bar) where 25 μM PINPS were incubated without Aβ. The data shows that a 1:50 molar ratio of PINPS:Aβ shows ~50% reduction in aggregate formation, and there is still some detectable inhibitory effect of the inhibitor even at a molar ratio of 1:5,000 (total lipids:Aβ) or 1:200,000 (RI-OR2-TAT:Aβ).

This is far more potent than any of the other Aβ aggregation inhibitors that the inventors have tested previously, and could not have been anticipated.

The fact that this result was unexpected is illustrated by data obtained for a curcumin derivative (another inhibitor of Aβ aggregation (30)) similarly attached to liposomes (i.e. in the form of click-curcumin liposomes). Click-curcumin liposomes did not show inhibition at such a high dilution and were only effective at 5:1, 2:1, 1:1 and 1:2 molar ratios of liposomes (total lipids):Aβ (30). In fact the click-curcumin liposomes actually stimulated Aβ aggregation at a 1:5 molar ratio of liposomes (total lipids):Aβ (30). This data is shown in a Table 2 below.

We have also tested a multivalent peptide dendrimer (data in table below) where four RI-OR2 peptide molecules were attached to a central moiety (based on the method described in reference 31). This dendrimer did not show any additional potency as an Aβ aggregation inhibitor when compared to RI-OR2 alone. The remarkable ability of the PINPs to inhibit aggregation at very low concentrations (high dilutions) cannot, therefore, be attributed solely to an effect of multivalency.

The data show that 50% inhibition of Aβ aggregation falls between the PINPS:Aβ molar ratios of 1:50 and 1:100. This high degree of potency of the PINPS was unexpected.

Table showing RFU values for the data presented in the figure above, along with standard deviation (SD). There are additional columns where the RFU for each of the conditions is presented as a percentage of that of Aβ alone (100% aggregation).

TABLE 1

| Condition | RFU at 48 hours | SD | % of control | SD |
|---|---|---|---|---|
| Neg control | 9095 | 208 | | |
| Aβ alone | 193027 | 7150 | 100 | |
| 1 to 1 PINPS:Aβ | 13817 | 268 | 7.1 | 0.139 |
| 1 to 5 | 14450 | 466 | 7.4 | 0.241 |
| 1 to 10 | 15664 | 832 | 8.1 | 0.431 |
| 1 to 50 | 85107 | 9992 | 44.0 | 5.17 |
| 1 to 100 | 132977 | 8675 | 68.8 | 4.49 |
| 1 to 500 | 165060 | 16375 | 85.5 | 8.48 |
| 1 to 1000 | 171555 | 24451 | 88.8 | 12.6 |
| 1 to 5000 | 148012 | 38730 | 76.6 | 20.0 |
| 1 to 10000 | 204059 | 8932 | 105 | 4.62 |
| 1 to 50000 | 199514 | 8398 | 103 | 4.35 |
| 1 to 100000 | 188616 | 31338 | 97.0 | 16.2 |
| Control liposomes | 9279 | 210 | | |

Table showing the RFU for Aβ (25 μM) alone, and Aβ incubated for 48 hrs with different molar ratios of click-curcumin liposomes:Aβ. See ref (30) for full details on the click-curcumin liposomes. Note that, unlike PINPs, these liposomes lose their ability to inhibit aggregation at the 1:5 molar ratio.

TABLE 2

| Condition | RFU at 48 hours | SD | % of control | SD |
|---|---|---|---|---|
| Aβ alone | 224563 | 19224 | 100 | |
| Click-curcumin liposomes 5:1 | 55835 | 27084 | 24 | 12 |
| Click-curcumin liposomes 2:1 | 125720 | 71881 | 55 | 32 |
| Click-curcumin liposomes 1:1 | 161135 | 29906 | 71 | 13 |
| Click-curcumin liposomes 1:2 | 198591 | 122845 | 88 | 54 |
| Click-curcumin liposomes 1:5 | 293951 | 47436 | 130 | 21 |

Table 3 shows unpublished thioflavin T data for the effects of a dendrimer, with four attached RI-OR2 molecules (prepared according to the method described in ref 31), on Aβ aggregation. The data show effects at different molar ratios of dendrimer:Aβ, with Aβ at 25 μM and incubation for 48 hrs. 'Dendrimer alone' refers to the central dendrimer scaffold with no inhibitor attached.

TABLE 3

| Condition | RFU at 48 hours | SD | % of control | SD |
|---|---|---|---|---|
| Aβ alone | 207856 | 12399 | 100 | |
| RI-OR2 1:2 | 72265 | 3379 | 35 | 1.6 |
| RI-OR2 dendrimer 1:1 | 169972 | 15968 | 82 | 7.7 |
| Dendrimer alone 1:1 | 239156 | 15452 | 115 | 7.4 |

EXAMPLE 10

This Example presents immunoassay data showing the ability of PINPs (derivatized with RI-OR2-TAT), at low concentrations, to inhibit Aβ oligomer formation This Example was carried out using the procedure described below. The results are shown in FIG. 12

Figure 12:
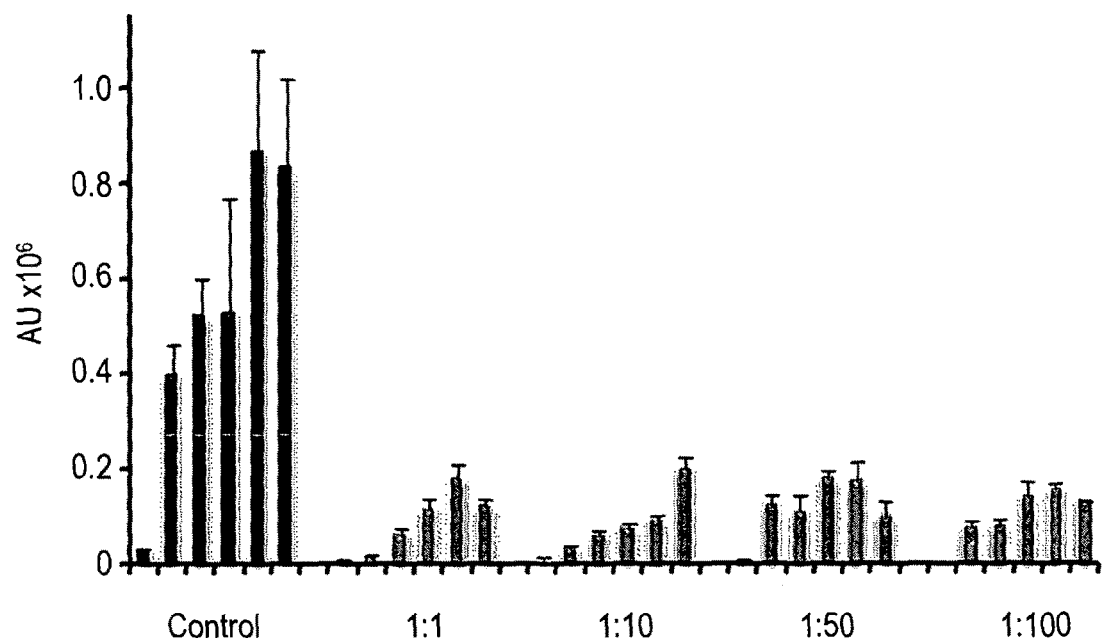
FIG. 12 shows immunoassay data for the effect of PINPs on Aβ oligomer formation.

FIG. 12 shows immunoassay data for the effect of PINPs on Aβ oligomer formation (tabulated below). The consecutive bars for each treatment indicate incubation of Aβ1-42 (at 12.5 μM) for 0, 2, 4, 8, 24 and 48 hours. It can be seen that Aβ1-42 alone aggregates into detectable oligomers even after 2 hours incubation. The inhibition of oligomer formation is still substantial at a 1:100 molar ratio of PINPS (total lipids):Aβ and is similar to that seen at the 1:1 molar ratio.

This is not the case with the peptide alone (i.e. RI-OR2 peptide), which loses its ability to inhibit oligomer formation at a 1:10 molar ratio of inhibitor:Aβ.

The sandwich immunoassay used follows the method described previously by Taylor et al (28, 30). Briefly, 96-well ELISA plates (Maxisorb) were coated with mouse monoclonal antibody 6E10 diluted 1:1000 in assay buffer (Tris-buffered saline (TBS), pH 7.4, containing 0.05% gamma globulins and 0.005% Tween 20). The incubated samples of peptide, with or without inhibitor (12.5 μM Aβ in 10 mM PB, and molar ratios of inhibitor:Aβ at 1:1, 1:10, 1:50 and 1:100), were diluted to 1 μM Aβ and incubated, in triplicate, in the 96-well plates for 1 hr at 37° C. The plates were washed with 10 mM phosphate-buffered saline (PBS), containing 0.5% Tween 20 (PBS-T). Following this, 100 μl of TBS containing a 1:1000 dilution of biotinylated 6E10 was added to each of the 96 wells and incubated for 1 hr at 37° C. After further washing, europium-linked streptavidin was added at 1:500 dilution in StrepE buffer (TBS containing, 20 μM DTPA, 0.5% bovine serum albumin and 0.05% gamma globulins) and again incubated for 1 hr and washed as before. Enhancer solution was added and the plates were read using the time-resolved fluorescence setting for europium on a Wallac Victor 2 plate reader.

Table 4 shows data presented in the bar chart of FIG. 12 above showing the effect of PINPs on aggregation of Aβ1-42 as measured by immunoassay. The data is shown as relative fluorescence units as measured in a time-resolved fluorescence assay for europium.

TABLE 4

| Time (hours) | Control Aβ alone | SD | PINPs 1:1 | SD | PINPs 1:10 | SD | PINPs 1:50 | SD | PINPs 1:100 | SD |
|---|---|---|---|---|---|---|---|---|---|---|
| 0 | 31275 | 2831 | 9494 | 1309 | 9666 | 3783 | 7833 | 1109 | 3766 | 663 |
| 2 | 395524 | 67114 | 17524 | 1985 | 33960 | 3336 | 124190 | 23321 | 78306 | 10983 |
| 4 | 522931 | 77147 | 62958 | 13486 | 63899 | 8314 | 111776 | 33546 | 82278 | 11443 |
| 8 | 523878 | 240936 | 116308 | 18173 | 77883 | 7708 | 177380 | 19314 | 141932 | 31278 |
| 24 | 866242 | 209791 | 178685 | 30820 | 95760 | 6412 | 173198 | 43652 | 154889 | 13489 |
| 48 | 833119 | 185629 | 122098 | 14704 | 198806 | 26442 | 99592 | 30617 | 131004 | 1957 |

EXAMPLE 11

Cell toxicity (MTT) assay showing that PINPs are not toxic to cells.

This Example was carried out using the procedure described in Section 13 of the Appendix. The results are shown in FIG. 13.

Figure 13:
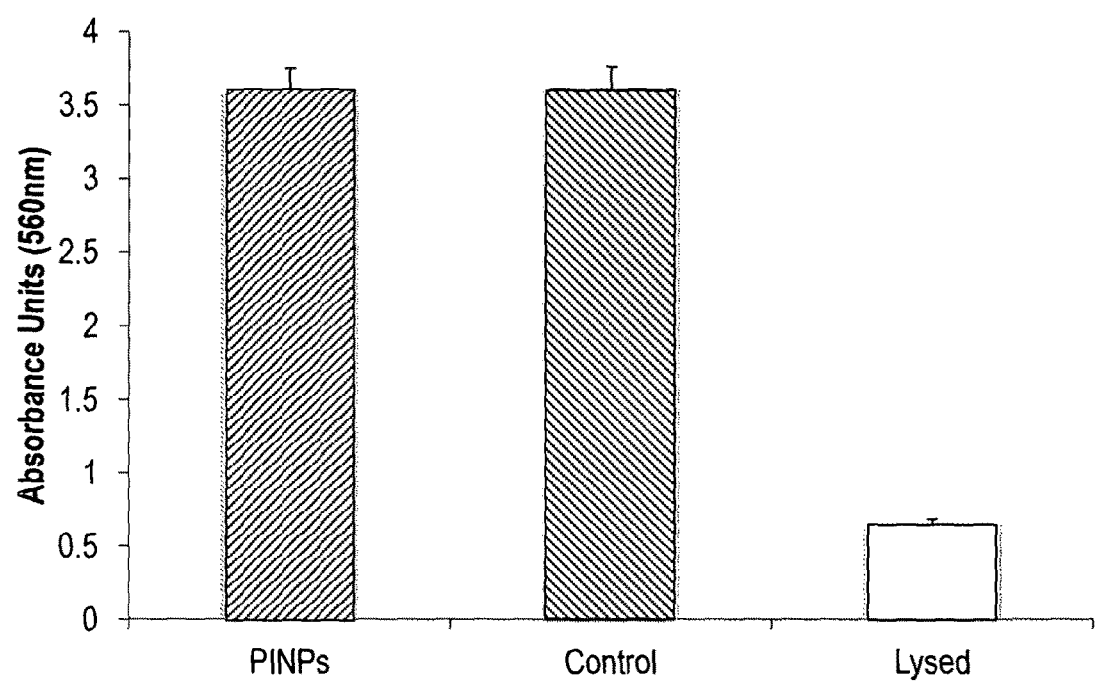
FIG. 13 shows the results of a cell toxicity (MTT) assay showing that PINPs are not toxic to cells.

FIG. 13 shows the effect of 10 μM PINPs on the viability of SHSY-5Y cells grown in culture (using an MTT cell toxicity assay, data in table below). It can be seen that there is no significant difference between cells grown in the presence or absence of the PINPs (labeled 'Control').

As a comparison, we also show data for cells that have been lysed, where the low absorbance value produced indicates the signal obtained from dead cells. The PINPs are, therefore, not toxic to cells at this concentration.

This lack of toxicity is a requirement for development of PINPs as a new drug therapy.

Table 5 shows the actual absorbance values for the data presented in the example above.

TABLE 5

| Condition | Absorbance units (560 nm) | Standard deviation |
|---|---|---|
| PINPs | 3.610 | 0.136 |
| Untreated cells | 3.608 | 0.151 |
| Lysed cells | 0.654 | 0.027 |

EXAMPLE 12

This Example provides cell toxicity data showing that PINPs protect cells from the toxic effects of Aβ1-42

Figure 14:
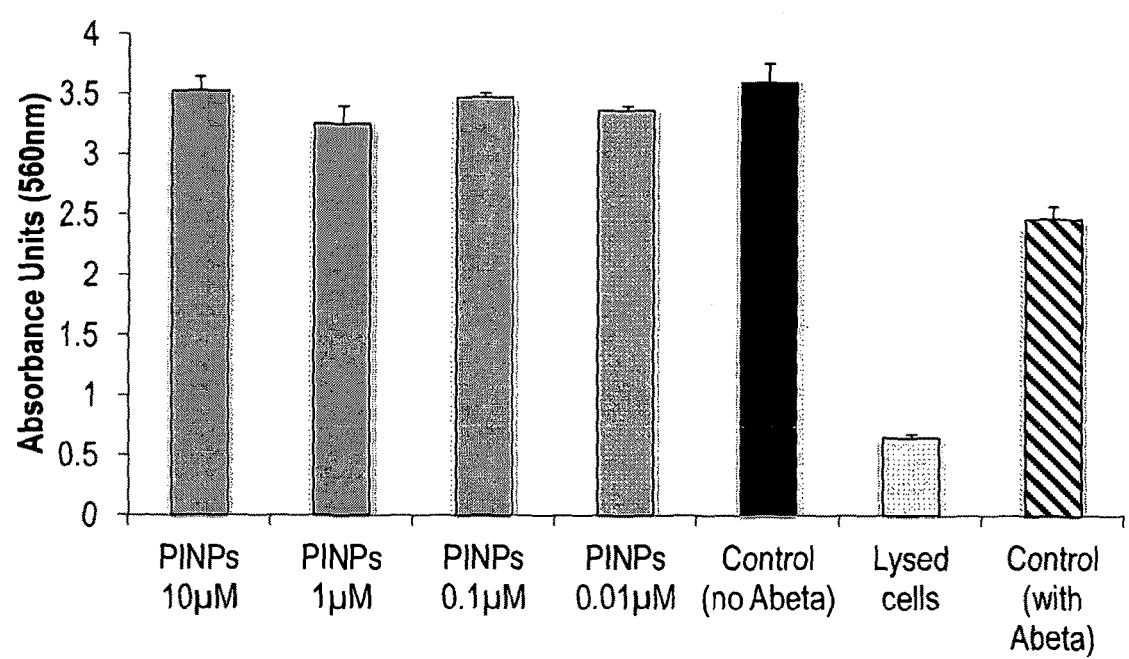
FIG. 14 provides cell toxicity data showing that PINPs protects cells from the toxic effects of Aβ 1-42.

The results for this Example are shown in FIG. 14.

FIG. 14 shows further cell viability data for SHSY-5Y cells grown in culture. In this case, the control cells (far right) were grown in the presence of pre-aggregated Aβ1-42. The bar labeled 'Lysed' shows data for 100% dead cells. The 'Liposome' bars (i.e. PINPs, at 10, 1, 0.1 0.01 μM) show data for cell viability assays when the cells were grown in the presence various concentrations of PINPs and pre-aggregated Aβ1-42. It can be seen that, for all of the concentration of PINPs indicated, cell viability remained near that of untreated cells, showing that the PINPs had a protective effect against the toxicity of Aβ1-42. The 'Control (Aβ)' bar shows an absorbance value below that of the untreated 'Control', indicated some degree of cell damage/death.

Table 6 shows the actual absorbance values for the data presented in the above example regarding the protective effect of PINPs on Aβ toxicity to SHSY 5Y cells grown in culture.

TABLE 6

| Condition | Absorption units (560 nm) | Standard deviation |
|---|---|---|
| PINPs 10 μM | 3.538 | 0.106 |
| PINPs 1 μM | 3.252 | 0.152 |
| PINPs 0.1 μM | 3.478 | 0.031 |
| PINPs 0.01 μM | 3.370 | 0.030 |
| Control (no Abeta) | 3.608 | 0.151 |
| Lysed cells | 0.654 | 0.027 |
| Control (with Abeta) | 2.467 | 0.101 |

APPENDIX

Methods

1. Peptides

All of the inhibitors used for this study were custom made by Cambridge Peptides (Birmingham, UK) and were >95% purity. Recombinant Aβ42, Ultrapure, was purchased from rPeptide, Bogart, Ga., USA. Prior to use for in vitro aggregation experiments, Aβ42 was deseeded [28]. The peptide was dissolved at 1 mgml in trifuoroacetic acid containing 4.5% thioanisol. After 1 h incubation at room temperature, all liquid was evaporated using a stream of oxygen-free nitrogen gas. The peptide was dissolved in 1,1,1,3,3,3-hexafluoro-2-propanol (HFIP) and this was then removed by centrifugation under vacuum. The latter process was repeated twice more before splitting the solution into smaller aliquots which were dried and stored at −20° C. until use.

2. Thioflavin T (ThT) Assay for Aβ Fibrils

This method was the same as that published previously [28]. Briefly, 60 μl samples of solutions containing Aβ42 (25 μM), ThT (15 μM) and between 0 and 125 μM RI-OR2 or RI-OR2-TAT, in 10 mM phosphate buffered saline (PBS), pH 7.4, were incubated in sealed, black, clear-bottomed 384-well plates (Corning). ThT fluorescence was monitored every 10 mins (λex=442 nm, λem=483 nm) for 48 h at 30° C. in a Biotek Synergy 2 plate reader.

3. Immunoassay for Aβ Oligomers (In Vitro)

This is a more sensitive test than the ThT assay for the detection of early oligomeric forms of Aβ [28]. Microtitre plates (96-well, Maxisorb) were coated with 6E10, diluted 1:1000 in 10 mM PBS, pH 7.4, for overnight at 4° C. The plates were blocked with assay buffer (Tris-buffered saline (TBS) (pH 7.4), containing 0.05% γ-globulins and 0.005% Tween 20) plus 5% gelatine for 1 h at 37° C. Samples of peptide (12.5 μM Aβ42 and 0, 3.125, 6.25, 12.5, 25 or 62.5 μM RI-OR2-TAT in 10 mM PBS, pH 7.4) were incubated at 25° C. for 0, 4, 8, 24 or 48 h, diluted to 1 μM Aβ, and plated in triplicate. The plates were incubated for 1 h at 37° C. and then washed with PBS plus 0.05% Tween-20 (PBST). A 1:1,000 dilution of biotinylated 6E10 was then added to each well, left for 1 h at 37° C., and the plates were washed with PBST. Europium-linked streptavidin was then added to the wells at 1:500 dilution in StrepE buffer (TBS containing 20 μM DTPA, 0.5% bovine serum albumin, and 0.05% γ-globulins), incubated for 1 h, and washed as before. Enhancer solution was added and the plates were read on a Wallac Victor 2 plate reader, using the time-resolved fluorescence setting for europium.

4. Cell Penetration and Cytotoxicity Experiments

For cell penetration experiments (Example 4), the fluorescein-tagged peptides were added to cell growth medium on a slide containing cultured SHSY-5Y cells at a concentration of 0.1 μM and micrographs were taken after 10 mins (Flu-RI-OR2-TAT) or 1 h (Flu-RI-OR2) incubations.

For cell toxicity assays (Example 3), SHSY-5Y neuroblastoma cells were maintained in 10% Fetal Calf Serum supplemented Dulbecco's Modified Eagle Medium (DMEM, Gibco) under standard mammalian cell culture conditions. The cells were transferred to sterile 96-well growth plates at 20,000 cells/well and 4 wells per condition. To test for any toxic effects of RI-OR2-TAT alone on the cells, they were left to adhere for 24 h before the addition of the inhibitor (at 12.5, 25, 50, 100 and 200 μM), in DMEM. To look at the ability of RI-OR2-TAT to protect against Aβ toxicity, the cell growth medium was changed to Optimem (Invitrogen) and Aβ42, pre-aggregated (at 100 μM) for 24 h at 25° C. in PBS, was added to the cells at a concentration of 5 µM, together with various amounts (0, 0.1, 0.5, 1, 5 or 10 µM) of RI-OR2-TAT. In each case, after a further 24 h incubation period, the viability of the cells was assessed using a CytoTox 96® Non-Radioactive Cytotoxicity Assay (LDH) Assay (Promega) kit.

5. Surface Plasmon Resonance (SPR)

These experiments were conducted using a Sensi Q semi-automatic SPR machine (ICx Nomadics). This apparatus has two parallel flow cells; one was used to immobilize Aβ42 fibrils while the other was used as "reference" (empty surface). A COOH5 sensor chip (ICx Nomadics) was employed for this purpose and the peptide was immobilized by amine coupling chemistry. Briefly, after surface activation, the peptide preparation was diluted to 10 µM in acetate buffer (pH 4.0) and then injected for 5 min at a flow rate of 30 µL/min. Any remaining activated groups were blocked with ethanolamine (pH 8.0). The final immobilization level was ~5,000 resonance units (1 RU=1 pg of protein/mm$^2$). The empty "reference" surface was prepared in parallel using the same immobilization procedure, but without addition of the peptide. Sensorgrams were then obtained via injection of three different concentrations of RI-OR2-TAT (1, 3 and 6 µM), as well as the vehicle (PBS with 0.005% Tween 20), over the immobilized ligand or control surface, in parallel.

These SPR data can be interpreted to provide an estimate for the affinity of binding of the inhibitors to Aβ fibrils [28,36].

6. Atomic force microscopy (AFM)

Aβ42 was incubated at 25 µM in the presence or absence of 12.5 µM RI-OR2-TAT in PBS, pH 7.4, for 24 h. Samples were diluted 1:10 in PBS and then a 2 µl aliquot was deposited onto the surface of freshly cleaned mica and allowed to dry.

Images were obtained in tapping mode using a Multimode™ SPM NanoScope IIIa microscope (Digital Instruments, New York, USA). Silicon cantilever tips measuring 125 µm long, 30 µm wide and with a tip radius <10 nm were used (Budget Sensors, Bulgaria). The resonance frequency was 300 kHz and force constants 40 Nm. All images were first order flattened and edited using WSxM 5.0 Develop 4.3 software, (Nanotech, Madrid, Spain) [37].

7. Animals

APPswe/PS1ΔE9 mice with a C57Bl/6 background (APP/PS1 mice) were obtained from the Jackson lab (http://research.iax.org/repository/alzheimers.html). To determine if Flu-RI-OR2-TAT crosses the blood brain barrier (Example 4), 2 male 17-months-old APP/PS1 animals and 2 16-months-old C57BL6 animals were used. To look at the effects of RI-OR2-TAT on mouse brain pathology (Example 5), 8 female 10-months-old APP/PS1 mice were used. The animals were housed in single cages in a temperature controlled holding room (21.5° C.±1) with 12:12 h light and dark cycle. Food and water was available ad libitum. All experiments were licensed by the UK Home Office in accordance with the UK animals (Scientific Procedures) Act 1986.

8. Drug Treatment

For Example 4, all 4 animals were injected i.p. with 100 nMol/Kg of Flu-RI-OR2-TAT in 0.9% NaCl at 0 h. The animals were then housed in a dark room. After 1 h, the animals were anaesthetised with isoflurane and sodium barbiturate (Dolethal, Bayer, Germany), transcardially perfused and the brains were retrieved and fixed in 4% ice cold paraformaldehyde.

For Example 5, 4 animals were injected intraperitonially (i.p.) with 0.9% NaCl (vehicle control) and the other 4 with RI-OR2-TAT (100 nMol/Kg in 0.9% NaCl) once daily, for 21 days. On the 22$^{nd}$ day, the animals were perfused transcardially with ice-cold PBS and 4% paraformaldehyde and then the brains were removed and post-fixed in 4% ice cold paraformaldehyde.

9. Immunostaining

All brains in paraformaldehyde were transferred to 30% sucrose overnight and then snap frozen with Envirofreez™ (Sigma, UK) and, using a Leica cryostat, 40 microns thick coronal sections were cut at anatomical regions of −2 to −3 bregma. Sections were preserved in cryoprotect with the first section taken at random and then every 5$^{th}$ section afterwards.

For Example 4, sections were incubated with a primary antibody to either Aβ (1:200 dilution, Invitrogen, 71-5800) or Iba 1 (1:1000 dilution, Wako 016-20001, Germany) at 4° C. overnight and then stained with goat anti-rabbit Alexa Fluor 555 (1:150 dilution, A21428 Invitrogen) for 1 h.

For Example 5, to stain for activated microglia, an inflammation response marker, sections were pretreated with 0.05 M sodium citrate buffer, pH 9, and incubated at 90° C. for 30 mins and stained with anti Iba-1 (1:2000 dilution, Wako 016-20001, Germany) [38]. For the oxidative stress marker, DNA denaturation was carried out with 2N HCl and the sections were stained for 8-oxo guanine (1:200 dilution, MAB3560, Millipore). Young immature neurons were detected by immunostaining for doublecortin (1:200 dilution, sc-66911, Santa Cruz Biotechnology). Total plaque load was quantified by immunostaining for β-amyloid (1:200 dilution, Invitrogen, 71-5800).

All sections were visualized using an Axio Scope 1 fluorescence microscope (Zeiss, Germany). For quantification, two images per section were taken from the cortex area with a 10× objective for 8-oxo guanine and β-amyloid staining, and a 100× objective for Iba1 staining, with a minimum of 5 sections visualized per animal. Image analysis was performed using multi threshold plug in Image J (NIH, USA).

For Example 4, sections were visualized using multichannel filters and images were merged using the microscope software.

10. ELISA Assay for Aβ Oligomer Analysis

Human oligomerised Aβ was measured using a kit purchased from Invitrogen, according to the manufacturer's instructions. Briefly, the right hemispheres from the brains of transgenic APP/PS1 mice treated with RI-OR2-TAT, or controls, were pooled separately and homogenized. Quantification of total protein was determined using the Bradford protein assay and was measured on a Nanophotometer (Implen, Germany). The homogenates were centrifuged at 100,000 g at 4° C. for 1 h. The supernatant was then diluted 1:10 before carrying out the sandwich ELISA, which measures soluble Aβ oligomer levels, but not amyloid monomers, as detailed in the manufacturer's protocol. The final AR oligomer values were determined following normalization of total protein levels.

11. Statistics

Figure 3:
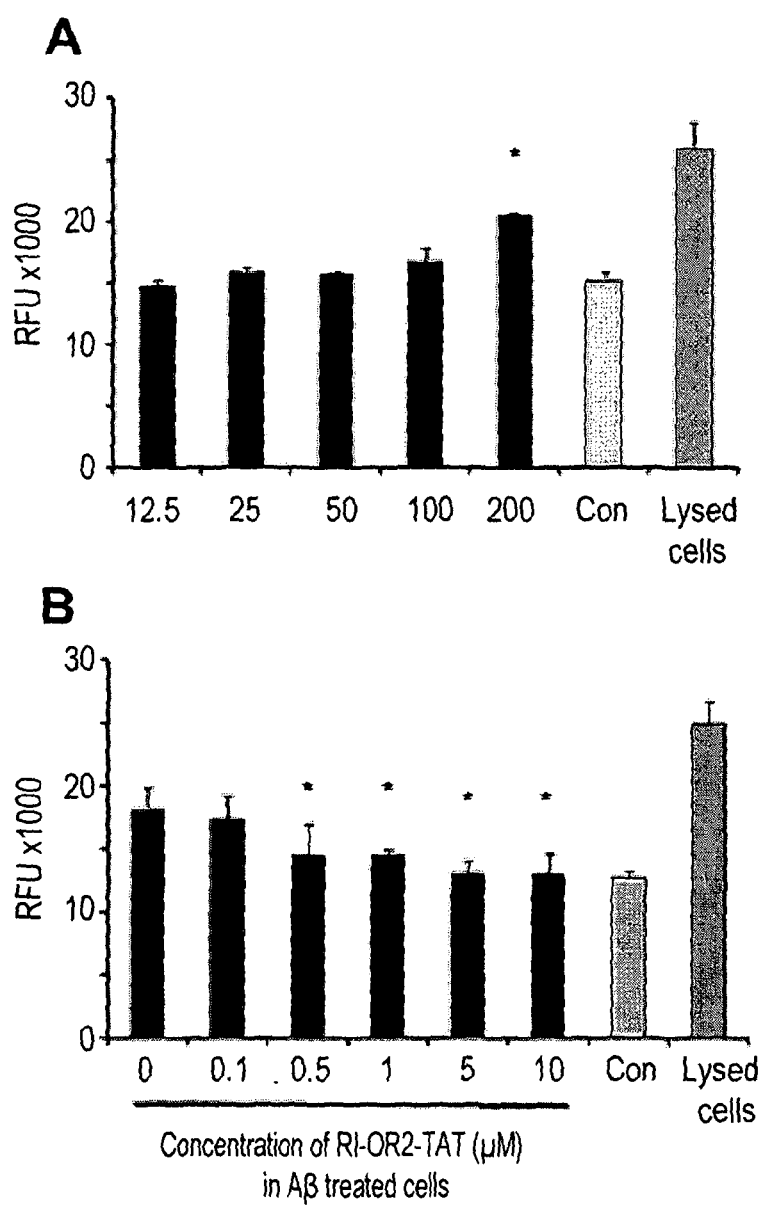
FIGS. 3A and B show that RI-OR2-TAT inhibits the toxic effects of Aβ42 on cells.

Statistical analysis in FIG. 5 and FIG. 6 was done using student t test, using GraphPad Prism software. All values were expressed as mean±SEM. A p-value of <0.05 was considered to be statistically significant. Statistical analysis as shown in FIG. 1 and FIG. 3 were also done using a student t test using Microsoft Excel. Values were expressed as a mean±SD.

12. Production of PINPS
   1. Into a 5 ml glass tube add:
      a. 1.067 mg of sphingomyelin
      b. 0.565 mg of cholesterol
      c. 0.07 mg of 1,2-dihexadecanoyl-sn-glycero-3-phosphoethanolamine-N-[4-(p-maleimidomethyl)cyclohexane-carboxamide
      d. This gives a molar ratio (a:b:c) of 47.5:47.5:5
   2. Resuspend the lipids in 25 µl of chloroform/methanol (2:1 v/v)
   3. Dry under a gentle stream of nitrogen gas
   4. Resuspend the dried lipid film in 1 ml phosphate buffered saline (PBS) pH 7.4 by vortexing
   5. Extrude the suspension through a 100 nm pore polycarbonate filer under 20 bar nitrogen pressure at room temperature ten times in order to create liposomes
   6. Transfer the resulting liposomes into a 5 ml glass tube and incubate with the peptide (e.g. 0.405 mg of RI-OR2 TAT in 150 µl of water) for two hours at 37° C.
   7. Incubate overnight at 4° C.
   8. To remove unbound peptide:
      a. Equilibrate a 25×1 cm column packed with Sepharose 4B-CL by passing 50 ml of PBS through the column
      b. Saturate the column with 1 ml of a 3 mM suspension of sphingomyelin/cholesterol liposomes (1:1 ratio)
      c. Apply the peptide liposome mixture to the column and collect 1 ml fractions
      d. Screen for the presence of liposomes in each fraction using Dynamic Light Scattering analysis (Malvern Instruments)
   9. Quantify the amount of protein present in the liposome fraction by protein estimation method e.g. Bradford Assay using Bovine Serum Albumin as a standard
13. MTT Cell Viability Assay.

SHSY 5Y cells were grown and maintained in DMEM (Dulbecco's Modified Eagle Medium) supplemented with FBS under standard mammalian cell culture conditions. During treatment cells were kept in Optimem plus or minus peptide liposomes in 96 well plates at 20000 cells per well for 24 hours, again under standard culture conditions. For cell protection assays 5 µM of pre-aggregated $A\beta_{1-42}$ was added at the same time as peptide liposomes. Cell viability was assessed for four wells for each treatment using a Promega CellTiter assay kit.

14. Surface Plasmon Resonance.

These experiments were conducted using a Sensi Q semi-automatic SPR machine (ICx Nomadics). This apparatus has two parallel flow cells; one was used to immobilize Aβ(1-42) fibrils (see Aβ peptides) while the other was used as "reference" (empty surface). A COOH5 sensor chip (ICx Nomadics) was employed for this purpose and the peptide was immobilized by amine coupling chemistry. Briefly, after surface activation, the peptide preparations was diluted to 10 µM in acetate buffer (pH 4.0) and then injected for 5 min at a flow rate of 30 µL/min. Any remaining activated groups were blocked with ethanolamine (pH 8.0). The final immobilization level was 5000 resonance units (1 RU=1 pg of protein/mm²). The empty "reference" surface was prepared in parallel using the same immobilization procedure, but without addition of the peptide. Sensorgrams were then obtained via injection of two different concentrations of RI-OR2 TAT/peptide liposome (1 and 3 µM), as well as the vehicle (PBS with 0.005% Tween 20), over the immobilized ligand or control surface, in parallel, at the same time.

REFERENCES

1. Brookmeyer, R., Gray, S. and Kawas, C. (1998) Projections of Alzheimer's disease in the United States and the public health impact of delaying disease onset. *Am. J. Public Health* 88, 1337-1342.
2. American Health Assistance Foundation. Alzheimer disease research: about Alzheimer. http:wwwahaforg/alzheimers/about 2000-2010.
3. Brookmeyer, R., Corrada, M. M., Curriero, F. C. and Kawas, C. (2002) Survival following a diagnosis of Alzheimer disease. *Arch. Neurol.* 59, 1764-1777.
4. Lambert, M. P., Barlow, A. K., Chromy, B. A., Edwards, C., Freed, R., Liosatos, M., Morgan, T. E., Rozovsky, I., Trommer, B., Viola, K. L., Wals, P., Zhang, C., Finch, C. E., Krafft, G. A., and Klein, W. L. (1998) Diffusible, nonfibrillar ligands derived from Aβ 1-42 are potent central nervous system neurotoxins. *Proc. Natl. Acad. Sci. USA* 95, 6448-6453.
5. Wang, H. W., Pasternak, J. F., Kuo, H., Ristic, H., Lambert, M. P., Chromy, B., Viola, K. L., Klein, W. L., Stine, W. B., Krafft, G. A., and Trommer, B. L. (2002) Soluble oligomers of β amyloid (1-42) inhibit long-term potentiation but not long-term depression in rat dentate gyrus. *Brain Res.* 924, 133-140.
6. Walsh, D. M., Klyubin, I., Fadeeva, J. V., Cullen, W. K., Anwyl, R., Wolfe, M. S., Rowan, M. J., and Selkoe, D. J. (2002) Naturally secreted oligomers of amyloid β protein potently inhibit hippocampal long-term potentiation in vivo. *Nature* 416, 535-539.
7. Kim, H. J., Chae, S. C., Lee, D. K., Chromy, B., Lee, S. C., Park, Y. C., Klein, W. L., Krafft, G. A., and Hong, S. T. (2003) Selective neuronal degeneration induced by soluble oligomeric amyloid β protein. *FASEB J* 17, 118-120.
8. Cleary, J. P., Walsh, D. M., Hofmeister, J. J., Shankar, G. M., Kuskowski, M. A., Selkoe, D. J., and Ashe, K. H. (2005) Natural oligomers of the amyloid-β protein specifically disrupt cognitive function. *Nature Neurosci.* 8, 79-84.
9. Walsh, D. M., and Selkoe, D. J. (2007) Aβ oligomers—a decade of discovery. *J. Neurochem.* 101, 1172-84.
10. Haass, C., and Selkoe, D. J. (2007) Soluble protein oligomers in neurodegeneration: lessons from the Alzheimer's amyloid β-peptide. *Nature Rev. Mol. Cell Biol.* 8, 101-12.
11. Citron M. (2010) Alzheimer's disease: strategies for disease modification. *Nat. Rev. Drug Discov.* 9, 387-398.
12. De Felice, F. G., Vieira, M. N., Saraiva, L. M., Figueroa-Villar, J. D., Garcia-Abreu, J., Liu, R., Chang, L., Klein, W. L., and Ferreira, S. T. (2004) Targeting the neurotoxic species in Alzheimer's disease: inhibitors of Aβ oligomerization. *FASEB J* 18, 1366-1372.
13. Siemers, E., DeMattos, R. B., May, P. C. and Dean, R. A. (2010) Role of biochemical Alzheimer's disease biomarkers as end points in clinical trials. *Biomark. Med.* 4, 81-89.
14. Yin, Y. I., Bassit, B., Zhu, L., Yang, X., Wang, C. and Li, Y. M. (2007) γ-Secretase substrate concentration modulates the Aβ42Aβ40 ratio: implications for Alzheimer disease. *J. Biol. Chem.* 282, 23639-23644.
15. DaSilva, K. A., Shaw, J. E., and McLaurin, J. (2010) Amyloid-β fibrillogenesis: structural insights and therapeutic intervention. Exp. Neurol. doi:10.1016j.expneurol.2009.08.032
16. Hawkes, C. A., Ng, V., and McLaurin, J. (2009) Small molecule inhibitors of Aβ aggregation and neurotoxicity. *Drug Dev. Res.* 69, 1-14.
17. Sciarretta, K. L., Gordon, D. J., and Meredith, S. C. (2006) Peptide-based inhibitors of amyloid assembly. *Methods Enzymol.* 413, 273-312.

18. Tjernberg, L. O., Naslund, J., Lindqvist, F., Johansson, J., Karlstrom, A. R., Thyberg, J., Terenius, L., and Nordstedt, C. (1996) Arrest of β-amyloid fibril formation by a pentapeptide ligand. J. Biol. Chem. 271, 8545-8548.
19. Tjernberg, L. O., Callaway, D. J. E., Tjernberg, A., Hahne, S., LilliehOOk, C., Terenius, L., Thyberg, J., and Nordstedt, C. (1999) A molecular model of Alzheimer amyloid β-peptide fibril formation. J. Biol. Chem. 274, 12619-12625.
20. Soto, C., Kindy, M. S., Baumann, M., and Frangione, B. (1996) Inhibition of Alzheimer's amyloidosis by peptides that prevent β-sheet conformation. Biochem. Biophys. Res. Commun. 226, 672-680.
21. Soto, C., Sigurdsson, E. M., Morelli, L., Kumar, R. A., Castano, E. M., and Frangione, B. (1998) Beta-sheet breaker peptides inhibit fibrillogenesis in a rat brain model of amyloidosis: implications for Alzheimer's therapy. Nature Med. 4, 822-826.
22. Gordon, D. J., Sciarretta, K. L., and Meredith, S. C. (2001) Inhibition of -amyloid (40) fibrillogenesis and disassembly of β-amyloid (40) fibrils by short -amyloid congeners containing N-methyl amino acids at alternate residues. Biochemistry 40, 8237-8245.
23. Kokkoni, N., Stott, K., Amijee, H., Mason, J. M., and Doig, A. J. (2006) N-Methylated peptide inhibitors of β-amyloid aggregation and toxicity. Optimization of the inhibitor structure. Biochemistry 45, 9906-9918.
24. Ghanta, J., Shen, C. L., Kiessling, L. L., and Murphy, R. M. (1996) A strategy for designing inhibitors of β-amyloid toxicity. J. Biol. Chem. 271, 29525-29528.
25. Poduslo, J. F., Curran, G. L., Kumar, A., Frangione, B., and Soto, C. (1999) β-sheet breaker peptide inhibitor of Alzheimer's amyloidogenesis with increased blood-brain barrier permeability and resistance to proteolytic degradation in plasma. J. Neurobiol. 39, 371-382.
26. Findeis, M. A., Musso, G. M., Arico-Muendel, C. C., Benjamin, H. W., Hundal, A. M., Lee, J. -J., Chin, J., Kelley, M., Wakefield, J., Hayward, N. J., and Molineaux, S. M. (1999) Modified-peptide inhibitors of amyloid β-peptide polymerization. Biochemistry 38, 6791-6800.
27. Austen, B. M., Paleologou, K. E., Sumaya, A., Ali, E., Qureshi, M. M., Allsop, D., and El-Agnaf, O. M. A. (2008) Designing peptide inhibitors for oligomerization and toxicity of Alzheimer's β-amyloid peptide. Biochemistry 47, 1984-1992.
28. Taylor, M., Moore, S., Mayes, J., Parkin, E., Beeg, M., Canovi, M., Gobbi, M., Mann, D. M. A. and Allsop, D. (2010) Development of a proteolytically stable retro-inverso peptide inhibitor of β-amyloid oligomerization as a potential novel treatment for Alzheimer's disease. Biochemistry 20, 3261-3272.
29. Lindsay, M. A. (2002) Peptide-mediated cell delivery: application in protein target validation. Current Opin. Pharmacol. 2, 587-594.
30. Taylor M., Moore S., Mourtas S., Niarakis A., Re F., Zona C., Ferla B., Nicotra F., Masserini M., Antimisiaris S. G., Gregori M. & Allsop D. (2011) Effect of curcumin-associated and lipid ligand functionalised nanoliposomes on aggregation of the Alzheimer's Aβ peptide. Nanomedicine (in press).
31. Chafekar, S. M., Malda, H., Merkx, M., Meijer, E. W., Viertl, D., Lashuel, H. A., Baas, F. & Scheper, W. (2007). Branched KLVFF tetramers strongly potentiate inhibition of β-amyloid aggregation. ChemBioChem 8, 1857-1864.
32. Simon, R. J et al., (1992) Peptoids: A modular approach to drug discovery. Proc. Natl. Acad. USA, 89, 9367-9371.
33. El-Agnaf, O. M. A., Paleologou, K. E., Greer, B., Abogrein, A. M., King, J. E., Salem, S. A., Fullwood, N. J., Benson, F. E., Hewitt, R., Ford, K. J., Martin, F. L., Harriott, P., Cookson, M. R. and Allsop, D. (2004) A strategy for designing inhibitors of α-synuclein aggregation and toxicity as a novel treatment for Parkinson's disease and related disorders. FASEB J. 18, 1315-1317.
34. Rehders, D., Claasen, B., Redecke, L., Buschke, A., Reibe, C., Jehmlich, N., von Bergen, M., Betzel, C. and Meyer, B. Peptide NMHRYPNQ of the cellular prion protein (PrP(C)) inhibits aggregation and is a potential key for understanding prion-prion interactions. J. Mol. Biol. 392, 198-207.
35. Goldsbury, C., Goldie, K., Pellaud, J., Seelig, J., Frey, P., Müller, S. A., Kistler, J., Cooper, G. J. and Aebi, U. (2000) Amyloid fibril formation from full-length and fragments of amylin. J. Struct. Biol. 130, 352-362.
36. Aguilar M I, Small D H (2005) Surface plasmon resonance for the analysis of 6-amyloid interactions and fibril formation in Alzheimer's disease research. Neurotox Res 7: 17-27.
37. Horcas I, Fernandez R, Gomez-Rodriquez J M, Colchero J, Gomez-Herrero J, et al (2007) WSXM: a software for scanning probe microscopy and a tool for nanotechnology. Rev Sci Instrum 78: 013705.
38. Imai Y, Kohsaka S (2002) Intracellular signaling in M-CSF-induced microglia activation: role of Iba1. Glia 40, 164-174.

The invention claimed is:

1. A composition comprising carrier particles each linked to a plurality of peptide constructs comprising a peptide binding sequence comprising a contiguous sequence of at least four D-amino acids from the sequence eaffvlkq and a transit amino acid sequence linked to said binding sequence, said binding sequence being capable of binding to an amyloid protein.

2. A composition as claimed in claim 1 wherein the amyloid protein is Aβ1-42.

3. A composition as claimed in claim 2 wherein the binding sequence is capable of binding to the sequence QKLVFFAE (SEQ ID NO. 1).

4. A composition as claimed in claim 1 wherein said binding sequence is a retroinverted D-peptide mimetic of an L-peptide sequence capable of binding to the amyloid protein.

5. A composition as claimed in claim 1 wherein the binding sequence comprises a contiguous sequence of at least five D-amino acids from the sequence eaffvlkq.

6. A composition as claimed in claim 5 wherein the binding sequence comprises a contiguous sequence of at least six D-amino acids from the sequence eaffvlkq.

7. A composition as claimed in claim 6 wherein the binding sequence comprises a contiguous sequence of at least seven D-amino acids from the sequence eaffvlkq.

8. A composition as claimed in claim 7 wherein the binding sequence comprises the sequence eaffvlkq.

9. A composition as claimed in claim 1 wherein the peptide construct additionally comprises amino acids Or attached at one end of the binding sequence via the G amino acid.

10. A composition as claimed in claim 1 wherein the peptide construct additionally comprises amino acids Or attached at each end of the binding sequence via the G amino acid.

11. A composition as claimed in claim 1 wherein the transit sequence is a retroinverted D-peptide mimetic of an L-peptide transit sequence.

12. A composition as claimed in claim 11 wherein the D-peptide transit sequence is a retroinverted D-peptide mimetic of the TAT peptide and has the sequence rrrqrrkkrGy.

13. A composition as claimed in claim 1 wherein the peptide construct comprises a maximum of 50 amino acids.

14. A composition as claimed in claim 1 wherein the peptide construct comprises the sequence rGffvlkGrrrrqrrkkrGy.

15. A composition as claimed in claim 1 wherein the carrier particles have a size in the range in the range 80-200 nm.

16. A composition as claimed in claim 1 wherein the carrier particles are liposomes.

17. A composition as claimed in claim 1 wherein individual carrier particles are bonded to at least 100 of said peptide constructs.

18. A composition as claimed in claim 1 in combination with a pharmaceutically acceptable vehicle.

19. A method of preventing and/or treating amyloid disease in a human or other mammalian patient comprising administering to a patient in need of such treatment a therapeutically effective amount of a composition as claimed in claim 1.

20. A method of preventing and/or treating amyloid aggregation in a human or other mammalian patient comprising administering to a patient in need of such treatment a therapeutically effective amount of a composition as claimed in claim 1.

21. A composition comprising liposomes to which are linked at least 100 peptide constructs having the sequence rGffvlkGrrrrqrrkkrGy.

* * * * *

SEQUENCE LISTING

<160> NUMBER OF SEQ ID NOS: 7

<210> SEQ ID NO 1
<211> LENGTH: 8
<212> TYPE: PRT
<213> ORGANISM: Unknown
<220> FEATURE:
<223> OTHER INFORMATION: Mammalian

<400> SEQUENCE: 1

Gln Lys Leu Val Phe Phe Ala Glu
1               5

<210> SEQ ID NO 2
<211> LENGTH: 9
<212> TYPE: PRT

```
<213> ORGANISM: Artificial Sequence
<220> FEATURE:
<223> OTHER INFORMATION: Artificial peptide-based inhibitor

<400> SEQUENCE: 2

Arg Gly Lys Leu Val Phe Phe Gly Arg
1               5

<210> SEQ ID NO 3
<211> LENGTH: 5
<212> TYPE: PRT
<213> ORGANISM: Unknown
<220> FEATURE:
<223> OTHER INFORMATION: Mammalian

<400> SEQUENCE: 3

Gly Ala Val Val Thr
1               5

<210> SEQ ID NO 4
<211> LENGTH: 8
<212> TYPE: PRT
<213> ORGANISM: Unknown
<220> FEATURE:
<223> OTHER INFORMATION: Prion protein

<400> SEQUENCE: 4

Asn Met His Arg Tyr Pro Asn Gln
1               5

<210> SEQ ID NO 5
<211> LENGTH: 6
<212> TYPE: PRT
<213> ORGANISM: Unknown
<220> FEATURE:
<223> OTHER INFORMATION: Mammalian

<400> SEQUENCE: 5

Phe Gly Ala Ile Leu Ser
1               5

<210> SEQ ID NO 6
<211> LENGTH: 11
<212> TYPE: PRT
<213> ORGANISM: Unknown
<220> FEATURE:
<223> OTHER INFORMATION: Viral TAT protein

<400> SEQUENCE: 6

Tyr Gly Arg Lys Lys Arg Arg Gln Arg Arg Arg
1               5                   10

<210> SEQ ID NO 7
<211> LENGTH: 5
<212> TYPE: PRT
<213> ORGANISM: Unknown
<220> FEATURE:
<223> OTHER INFORMATION: Mammalian

<400> SEQUENCE: 7

Lys Leu Val Phe Phe
1               5
```